(12) United States Patent
Franklin et al.

(10) Patent No.: US 11,185,641 B2
(45) Date of Patent: Nov. 30, 2021

(54) DEVICES FOR INJECTION AND DOSING

(71) Applicant: Allergan, Inc., Irvine, CA (US)

(72) Inventors: Ethan Franklin, Santa Barbara, CA (US); Dimitrios Stroumpoulis, Goleta, CA (US); Zachary Dominguez, Santa Barbara, CA (US); Justin Schwab, San Francisco, CA (US); Bastien Mandaroux, Cran Gevrier (FR); Edwin Kayda, Santa Barbara, CA (US)

(73) Assignee: ALLERGAN, INC., Irvine, CA (US)

( * ) Notice: Subject to any disclaimer, the term of this patent is extended or adjusted under 35 U.S.C. 154(b) by 114 days.

(21) Appl. No.: 16/299,029

(22) Filed: Mar. 11, 2019

(65) Prior Publication Data

US 2019/0201635 A1    Jul. 4, 2019

Related U.S. Application Data

(63) Continuation of application No. 14/852,903, filed on Sep. 14, 2015, now Pat. No. 10,226,585.
(Continued)

(51) Int. Cl.
*A61M 5/32*    (2006.01)
*A61M 5/20*    (2006.01)
(Continued)

(52) U.S. Cl.
CPC ........... *A61M 5/3298* (2013.01); *A61M 5/19* (2013.01); *A61M 5/204* (2013.01);
(Continued)

(58) Field of Classification Search
CPC ........ A61M 5/3298; A61M 2037/0023; A61M 2037/003; A61M 2037/0061; A61M 5/3295; A61M 37/0015
See application file for complete search history.

(56) References Cited

U.S. PATENT DOCUMENTS

| 1,250,114 A | 12/1917 | Bigelow et al. |
| 1,558,037 A | 10/1925 | Morton |

(Continued)

FOREIGN PATENT DOCUMENTS

| CN | 2535071 | 2/2003 |
| CN | 200960353 | 10/2007 |

(Continued)

OTHER PUBLICATIONS

Bleyer, "Sis Facial Implant 510(k) Summary," Cook Biotech Inc., May 2005, 1 page.
(Continued)

*Primary Examiner* — Nathan R Price
*Assistant Examiner* — Courtney B Fredrickson
(74) *Attorney, Agent, or Firm* — Nathan S. Smith; Sujohn Das; Morgan, Lewis & Bockius LLP

(57) ABSTRACT

Skin can be treated by piercing skin with a plurality of needles of an injection device and ejecting a dose of fluid therethrough. The device can include a housing, a plunger disposed in the housing, a cartridge disposed in the housing, and one or more dosing chambers. The plurality of needles can be coupled to the housing and be in fluid communication with the cartridge. Advancement of the plunger can cause a dose of fluid to be ejected from the plurality of needles.

12 Claims, 15 Drawing Sheets

Related U.S. Application Data

(60) Provisional application No. 62/058,587, filed on Oct. 1, 2014, provisional application No. 62/187,077, filed on Jun. 30, 2015.

(51) Int. Cl.
    *A61M 5/315*     (2006.01)
    *A61M 5/19*     (2006.01)
    *A61M 37/00*     (2006.01)

(52) U.S. Cl.
    CPC .... *A61M 5/31581* (2013.01); *A61M 5/31593* (2013.01); *A61M 5/321* (2013.01); *A61M 5/326* (2013.01); *A61M 5/3287* (2013.01); *A61M 37/0015* (2013.01)

(56) References Cited

U.S. PATENT DOCUMENTS

| | | |
|---|---|---|
| 1,591,021 A | 7/1926 | Davis |
| 2,007,140 A | 7/1935 | Ragnar |
| 2,302,986 A | 11/1942 | Vollrath |
| 2,491,978 A | 12/1949 | Helfman |
| 2,551,902 A | 5/1951 | Rieck |
| 2,737,946 A | 3/1956 | Hein, Jr. |
| 2,853,070 A | 9/1958 | Julliard |
| 3,086,530 A | 4/1963 | Groom |
| 3,161,323 A | 12/1964 | Bent |
| D202,754 S | 11/1965 | Fnftolin |
| D214,112 S | 5/1969 | Langdon |
| 3,517,668 A | 6/1970 | Brickson |
| 3,595,231 A | 7/1971 | Pistor |
| D224,066 S | 6/1972 | McDonald |
| 3,720,211 A | 3/1973 | Kyrias |
| 3,767,085 A | 10/1973 | Cannon et al. |
| 3,807,048 A | 4/1974 | Malmin |
| 3,910,282 A | 10/1975 | Messer et al. |
| 3,916,777 A | 11/1975 | Earl |
| 4,064,879 A | 12/1977 | Leibinsohn |
| 4,240,423 A | 12/1980 | Akhavi |
| 4,240,426 A | 12/1980 | Akhavi |
| 4,273,122 A | 6/1981 | Whitney et al. |
| 4,326,517 A | 4/1982 | Whitney et al. |
| 4,346,708 A | 8/1982 | Leeven |
| 4,444,560 A | 4/1984 | Jacklich |
| 4,529,401 A | 7/1985 | Leslie et al. |
| 4,617,016 A | 10/1986 | Blomberg |
| 4,624,659 A | 11/1986 | Goldberg |
| 4,671,255 A | 6/1987 | Dubrul et al. |
| 4,695,273 A | 9/1987 | Brown |
| 4,699,612 A | 10/1987 | Hamacher |
| 4,710,172 A | 12/1987 | Jacklich |
| 4,719,918 A | 1/1988 | Bonomo et al. |
| 4,755,169 A | 7/1988 | Samoff |
| 4,759,750 A | 7/1988 | Devries |
| 4,800,901 A | 1/1989 | Rosenberg |
| 4,832,692 A | 5/1989 | Box |
| 4,841,948 A | 6/1989 | Bauser et al. |
| 4,841,992 A | 6/1989 | Sasaki et al. |
| 4,846,886 A | 7/1989 | Fey et al. |
| D303,010 S | 8/1989 | Jabbusch |
| 4,869,717 A | 9/1989 | Adair |
| 4,908,029 A | 3/1990 | Bark et al. |
| 4,955,905 A | 9/1990 | Reed |
| 4,957,744 A | 9/1990 | dellaValle et al. |
| 5,024,656 A | 6/1991 | Gasaway et al. |
| 5,046,506 A | 9/1991 | Singer |
| 5,066,303 A | 11/1991 | Bark et al. |
| 5,092,348 A | 3/1992 | Dubrul et al. |
| 5,100,390 A | 3/1992 | Lubeck et al. |
| 5,104,375 A | 3/1992 | Lubeck et al. |
| 5,116,358 A | 5/1992 | Granger et al. |
| 5,127,436 A | 7/1992 | Campion et al. |
| 5,141,496 A | 8/1992 | Daito et al. |
| 5,211,644 A | 5/1993 | VanBeek et al. |
| 5,258,013 A | 11/1993 | Granger et al. |
| 5,270,685 A | 12/1993 | Hagen |
| 5,279,544 A | 1/1994 | Gross |
| 5,295,980 A | 3/1994 | Ersek |
| 5,305,788 A | 4/1994 | Mayeux |
| 5,318,544 A | 6/1994 | Drypen |
| 5,322,511 A | 6/1994 | Armbruster et al. |
| 5,344,407 A | 9/1994 | Ryan |
| 5,354,279 A | 10/1994 | Hofling |
| 5,368,572 A | 11/1994 | Shirota |
| 5,383,851 A | 1/1995 | Mackinnon, Jr. |
| 5,405,330 A | 4/1995 | Zunitch et al. |
| 5,433,352 A | 7/1995 | Ronvig |
| 5,478,327 A | 12/1995 | McGregor et al. |
| 5,540,657 A | 7/1996 | Kurjan |
| 5,549,672 A | 8/1996 | Maddock et al. |
| 5,611,809 A | 3/1997 | Marshall et al. |
| D378,939 S | 4/1997 | Smith et al. |
| 5,690,618 A | 11/1997 | Smith et al. |
| 5,752,970 A | 5/1998 | Yoon |
| 5,807,340 A | 9/1998 | Pokras |
| 5,817,033 A | 10/1998 | DeSantis |
| 5,824,335 A | 10/1998 | Dorigatti et al. |
| 5,846,225 A | 12/1998 | Rosengart et al. |
| 5,941,845 A | 8/1999 | Tu et al. |
| 5,964,737 A | 10/1999 | Caizza |
| D424,194 S | 5/2000 | Holdaway et al. |
| 6,077,251 A | 6/2000 | Ting et al. |
| 6,102,929 A | 8/2000 | Conway et al. |
| 6,159,233 A | 12/2000 | Matsuzawa |
| 6,171,276 B1 | 1/2001 | Lippe |
| 6,183,434 B1 | 2/2001 | Eppstein |
| D441,077 S | 4/2001 | Garito et al. |
| 6,231,552 B1 | 5/2001 | Jentzen |
| 6,231,570 B1 | 5/2001 | Tu et al. |
| 6,283,951 B1 | 9/2001 | Flaherty et al. |
| 6,293,925 B1 | 9/2001 | Safabash et al. |
| 6,303,518 B1 | 10/2001 | Aceti |
| 6,312,412 B1 | 11/2001 | Saied |
| 6,432,046 B1 | 8/2002 | Yarush et al. |
| 6,451,240 B1 | 9/2002 | Sherman et al. |
| 6,482,187 B1 | 11/2002 | Gibbs |
| 6,488,651 B1 | 12/2002 | Morris |
| 6,551,290 B1 | 4/2003 | Elsberry et al. |
| 6,595,960 B2 | 7/2003 | West et al. |
| 6,607,512 B2 | 8/2003 | Oliver |
| 6,607,513 B1 | 8/2003 | Down |
| 6,611,707 B1 | 8/2003 | Prausnitz et al. |
| 6,613,010 B2 | 9/2003 | Castellano |
| 6,616,448 B2 | 9/2003 | Friedman |
| D483,116 S | 12/2003 | Castellano |
| 6,689,095 B1 | 2/2004 | Garitano et al. |
| 6,689,103 B1 | 2/2004 | Palasis |
| 6,780,171 B2 | 8/2004 | Gabel |
| 6,783,514 B2 | 8/2004 | Tovey et al. |
| 6,824,526 B2 | 11/2004 | Castellano |
| 6,896,666 B2 | 5/2005 | Kochamba |
| 6,901,850 B2 | 6/2005 | Corominas |
| 6,908,453 B2 | 6/2005 | Fleming |
| 6,936,297 B2 | 8/2005 | Roby et al. |
| 6,945,952 B2 | 9/2005 | Kwon |
| 7,004,928 B2 | 2/2006 | Aceti |
| 7,018,356 B2 | 3/2006 | Wise et al. |
| 7,033,337 B2 | 4/2006 | Hjertman |
| 7,041,088 B2 | 5/2006 | Nawrocki et al. |
| 7,047,070 B2 | 5/2006 | Wilkinson et al. |
| 7,048,729 B2 | 5/2006 | Meglin et al. |
| 7,097,631 B2 | 8/2006 | Trautman |
| 7,108,681 B2 | 9/2006 | Gartstein |
| 7,115,108 B2 | 10/2006 | Wilkinson et al. |
| 7,150,726 B2 | 12/2006 | Dalton |
| 7,302,885 B2 | 12/2007 | Townsend |
| 7,361,163 B2 | 4/2008 | Cohen |
| 7,419,472 B2 | 9/2008 | Hibner et al. |
| 7,442,187 B2 | 10/2008 | Khayal et al. |
| 7,494,473 B2 | 2/2009 | Eggers et al. |
| 7,504,386 B2 | 3/2009 | Pressato et al. |
| 7,556,615 B2 | 7/2009 | Pettis et al. |
| 7,559,952 B2 | 7/2009 | Pinchuck |

(56) References Cited

U.S. PATENT DOCUMENTS

| | | |
|---|---|---|
| 7,588,547 B2 | 9/2009 | Deem |
| 7,611,495 B1 | 11/2009 | Gianturco |
| 7,651,475 B2 | 1/2010 | Angel |
| 7,662,110 B2 | 2/2010 | Flaherty |
| 7,664,545 B2 | 2/2010 | Westersten et al. |
| 7,666,339 B2 | 2/2010 | Chaouk et al. |
| D615,192 S | 5/2010 | Mudd et al. |
| 7,722,582 B2 | 5/2010 | Lina et al. |
| 7,762,983 B2 | 7/2010 | Amissolle |
| 7,850,656 B2 | 12/2010 | McKay et al. |
| 7,850,683 B2 | 12/2010 | Elkins |
| 7,878,981 B2 | 2/2011 | Strother et al. |
| 7,896,837 B2 | 3/2011 | Wilkinson et al. |
| D637,287 S | 5/2011 | Mudd et al. |
| 7,998,170 B2 | 8/2011 | Cunningham |
| 8,012,139 B2 | 9/2011 | McKay et al. |
| 8,029,460 B2 | 10/2011 | Rush et al. |
| 8,066,629 B2 | 11/2011 | Dlugos |
| 8,083,722 B2 | 12/2011 | McKay et al. |
| 8,088,108 B2 | 1/2012 | Kraft |
| 8,157,830 B2 | 4/2012 | Wenchell |
| 8,172,815 B2 | 5/2012 | Down et al. |
| 8,216,190 B2 | 7/2012 | Gartstein |
| 8,236,021 B2 | 8/2012 | Kluge |
| 8,291,768 B2 | 10/2012 | Spiegel |
| 8,303,518 B2 | 11/2012 | Aceti |
| 8,303,545 B2 | 11/2012 | Schraga |
| 8,343,132 B2 | 1/2013 | Heneveld et al. |
| 8,349,554 B2 | 1/2013 | Bahrami et al. |
| 8,353,871 B2 | 1/2013 | Zimmerman |
| 8,366,643 B2 | 2/2013 | Deem |
| 8,394,118 B2 | 3/2013 | Jones et al. |
| 8,409,147 B2 | 4/2013 | Kraft |
| 8,409,185 B2 | 4/2013 | Burger |
| 8,480,630 B2 | 7/2013 | Mudd et al. |
| 8,535,278 B2 | 9/2013 | Mudd et al. |
| 8,562,571 B2 | 10/2013 | Mudd et al. |
| 8,603,028 B2 | 12/2013 | Mudd et al. |
| 8,632,501 B2 | 1/2014 | Kraft |
| 8,636,797 B2 | 1/2014 | Chitre et al. |
| 8,657,786 B2 | 2/2014 | Bahrami et al. |
| 8,668,675 B2 | 3/2014 | Chase |
| 8,708,965 B2 | 4/2014 | Boyden |
| 8,712,815 B1 | 4/2014 | Nichols et al. |
| 8,821,446 B2 | 9/2014 | Trautman |
| 8,900,181 B2 | 12/2014 | Knowlton |
| 8,900,186 B2 | 12/2014 | Pettis et al. |
| 8,945,060 B2 | 2/2015 | Bunch |
| 9,017,289 B2 | 4/2015 | Backes |
| 9,017,318 B2 | 4/2015 | Fourkas |
| 9,039,688 B2 | 5/2015 | Palmer, III |
| 9,066,712 B2 | 6/2015 | Fourkas |
| 9,072,498 B2 | 7/2015 | Elkins |
| 9,101,346 B2 | 8/2015 | Burger |
| 9,113,855 B2 | 8/2015 | Burger |
| 9,149,331 B2 | 10/2015 | Deem |
| 9,155,584 B2 | 10/2015 | Fourkas |
| 9,180,273 B2 | 11/2015 | Konstantino |
| 9,214,030 B2 | 12/2015 | Sole et al. |
| 9,227,023 B2 | 1/2016 | Kraft |
| 9,241,753 B2 | 1/2016 | Fourkas |
| 9,254,162 B2 | 2/2016 | Burger |
| 9,289,605 B2 | 3/2016 | Choi |
| 9,314,568 B2 | 4/2016 | Gurtner et al. |
| 9,468,748 B2 | 10/2016 | Bang |
| 2001/0008937 A1 | 7/2001 | Callegaro et al. |
| 2002/0010433 A1 | 1/2002 | Johnson |
| 2002/0026039 A1 | 2/2002 | Bellini et al. |
| 2002/0065483 A1 | 5/2002 | Leon |
| 2002/0133114 A1 | 9/2002 | Itoh |
| 2002/0151843 A1 | 10/2002 | Correa et al. |
| 2003/0028154 A1 | 2/2003 | Ros |
| 2003/0050602 A1* | 3/2003 | Pettis ............. A61M 5/46 604/117 |
| 2003/0078912 A1 | 4/2003 | Oliver |
| 2003/0144632 A1 | 7/2003 | Hommann et al. |
| 2003/0181863 A1 | 9/2003 | Ackley |
| 2003/0199883 A1 | 10/2003 | Laks |
| 2004/0010224 A1 | 1/2004 | Bodmeier |
| 2004/0015133 A1 | 1/2004 | Karim |
| 2004/0092927 A1 | 5/2004 | Podhajsky et al. |
| 2004/0147883 A1 | 7/2004 | Tsai |
| 2004/0192643 A1 | 9/2004 | Pressato et al. |
| 2004/0220532 A1 | 11/2004 | Caizza |
| 2005/0033362 A1 | 2/2005 | Grafton |
| 2005/0085767 A1 | 4/2005 | Menassa |
| 2005/0131346 A1* | 6/2005 | Douglas ............. A61M 5/158 604/136 |
| 2005/0131353 A1 | 6/2005 | Mossanen-Shams et al. |
| 2005/0137496 A1 | 7/2005 | Walsh et al. |
| 2005/0177117 A1 | 8/2005 | Crocker et al. |
| 2005/0182446 A1 | 8/2005 | DeSantis |
| 2005/0215956 A1 | 9/2005 | Nerney |
| 2005/0261633 A1 | 11/2005 | Khalaj |
| 2006/0041320 A1 | 2/2006 | Matsuda |
| 2006/0079765 A1 | 4/2006 | Neer |
| 2006/0089594 A1 | 4/2006 | Landau |
| 2006/0150742 A1 | 7/2006 | Esnouf |
| 2006/0178631 A1* | 8/2006 | Gillespie ............. A61M 5/286 604/139 |
| 2007/0038181 A1 | 2/2007 | Melamud |
| 2007/0083155 A1 | 4/2007 | Muller |
| 2007/0085767 A1 | 4/2007 | Menassa |
| 2007/0100363 A1 | 5/2007 | Dollar et al. |
| 2007/0167920 A1 | 7/2007 | Hommann |
| 2007/0212385 A1 | 9/2007 | David |
| 2007/0250010 A1 | 10/2007 | Hohlfelder et al. |
| 2007/0270710 A1 | 11/2007 | Frass et al. |
| 2008/0015522 A1 | 1/2008 | Yeshurun |
| 2008/0033347 A1 | 2/2008 | D'Arrigo et al. |
| 2008/0058706 A1 | 3/2008 | Zhang |
| 2008/0058839 A1 | 3/2008 | Nobles |
| 2008/0071385 A1 | 3/2008 | Binette et al. |
| 2008/0097325 A1 | 4/2008 | Tanaka et al. |
| 2008/0108952 A1 | 5/2008 | Horvath et al. |
| 2008/0114305 A1 | 5/2008 | Gerondale |
| 2008/0119797 A1 | 5/2008 | Kim |
| 2008/0119876 A1 | 5/2008 | Price et al. |
| 2008/0161772 A1 | 7/2008 | Nayak |
| 2008/0167674 A1 | 7/2008 | Bodduluri et al. |
| 2008/0188816 A1 | 8/2008 | Shimazaki |
| 2008/0200758 A1 | 8/2008 | Orbay et al. |
| 2008/0281278 A1 | 11/2008 | Williams |
| 2009/0088703 A1 | 4/2009 | Azar |
| 2009/0124996 A1 | 5/2009 | Heneveld et al. |
| 2009/0125050 A1 | 5/2009 | Dixon |
| 2009/0143746 A1 | 6/2009 | Mudd et al. |
| 2009/0187118 A1 | 7/2009 | Kim |
| 2009/0234322 A1 | 9/2009 | Fischer |
| 2009/0240200 A1 | 9/2009 | Heneveld et al. |
| 2009/0247953 A1 | 10/2009 | Yeshurun |
| 2009/0259180 A1 | 10/2009 | Choi |
| 2009/0275917 A1 | 11/2009 | Azar |
| 2009/0287161 A1 | 11/2009 | Traub |
| 2009/0299328 A1 | 12/2009 | Mudd et al. |
| 2010/0006095 A1 | 1/2010 | Woodcock |
| 2010/0030152 A1 | 2/2010 | Lee et al. |
| 2010/0069848 A1 | 3/2010 | Alferness |
| 2010/0100114 A1 | 4/2010 | Berger |
| 2010/0121307 A1* | 5/2010 | Lockard ............. A61M 37/0015 604/506 |
| 2010/0152675 A1 | 6/2010 | McClintock |
| 2010/0152679 A1 | 6/2010 | Tezel |
| 2010/0179488 A1 | 7/2010 | Spiegel |
| 2010/0256594 A1 | 10/2010 | Kimmell |
| 2010/0256596 A1 | 10/2010 | Chomas |
| 2010/0280488 A1 | 11/2010 | Pruiitt et al. |
| 2010/0282774 A1 | 11/2010 | Greter et al. |
| 2010/0286618 A1 | 11/2010 | Choi |
| 2011/0009808 A1 | 1/2011 | AlGhamdi |
| 2011/0021905 A1 | 1/2011 | Patrick et al. |
| 2011/0028910 A1 | 2/2011 | Weber |
| 2011/0092883 A1* | 4/2011 | Uchiyama ............. A61M 37/0015 604/21 |

(56) References Cited

U.S. PATENT DOCUMENTS

| | | |
|---|---|---|
| 2011/0092916 A1 | 4/2011 | Tezel et al. |
| 2011/0137286 A1 | 6/2011 | Mudd et al. |
| 2011/0152926 A1 | 6/2011 | Vetrecin |
| 2011/0160674 A1 | 6/2011 | Holmes et al. |
| 2011/0172645 A1 | 7/2011 | Moga |
| 2011/0190974 A1 | 8/2011 | Holmes et al. |
| 2011/0202014 A1 | 8/2011 | Mutzbauer |
| 2011/0218494 A1 | 9/2011 | Assaf |
| 2011/0218497 A1 | 9/2011 | Assaf |
| 2011/0230839 A1 | 9/2011 | Bahrami et al. |
| 2011/0238038 A1 | 9/2011 | Sefi |
| 2011/0263724 A1 | 10/2011 | Gurtner |
| 2011/0319865 A1 | 12/2011 | Buss |
| 2012/0041374 A1 | 2/2012 | Lee |
| 2012/0089211 A1 | 4/2012 | Curtis |
| 2012/0101475 A1 | 4/2012 | Wilmot |
| 2012/0123194 A1 | 5/2012 | Beckman |
| 2012/0123537 A1 | 5/2012 | Manesis et al. |
| 2012/0141532 A1 | 6/2012 | Blanda et al. |
| 2012/0150266 A1 | 6/2012 | Shalev |
| 2012/0245629 A1 | 9/2012 | Gross et al. |
| 2012/0259322 A1 | 10/2012 | Fourkas |
| 2012/0265064 A1 | 10/2012 | Bahrami et al. |
| 2012/0265171 A1 | 10/2012 | Thome |
| 2012/0296206 A1 | 11/2012 | Bahrami et al. |
| 2013/0012865 A1 | 1/2013 | Sallberg et al. |
| 2013/0041346 A1 | 2/2013 | Alon |
| 2013/0096531 A1 | 4/2013 | Estepa et al. |
| 2013/0122068 A1 | 5/2013 | Fermanian et al. |
| 2013/0131632 A1 | 5/2013 | Mudd et al. |
| 2013/0131633 A1 | 5/2013 | Mudd et al. |
| 2013/0150826 A1 | 6/2013 | Almohizea |
| 2013/0184648 A1 | 7/2013 | Inou et al. |
| 2013/0184696 A1 | 7/2013 | Fourkas |
| 2013/0197446 A1 | 8/2013 | Gustafsson |
| 2013/0197449 A1 | 8/2013 | Franklin et al. |
| 2013/0211374 A1 | 8/2013 | Hetherington |
| 2013/0253289 A1 | 9/2013 | Hadvary |
| 2013/0274655 A1 | 10/2013 | Jennings |
| 2013/0274670 A1 | 10/2013 | Mudd et al. |
| 2013/0280755 A1 | 10/2013 | Hubert |
| 2013/0310763 A1 | 11/2013 | Mudd et al. |
| 2014/0018770 A1 | 1/2014 | Sutkin |
| 2014/0018835 A1 | 1/2014 | Scherkowski |
| 2014/0066845 A1 | 3/2014 | Mudd et al. |
| 2014/0088502 A1 | 3/2014 | Matheny et al. |
| 2014/0088553 A1 | 3/2014 | Hetherington |
| 2014/0114279 A1 | 4/2014 | Klinghoffer |
| 2014/0121587 A1 | 5/2014 | Sallberg et al. |
| 2014/0128685 A1 | 5/2014 | Na |
| 2014/0128810 A1 | 5/2014 | Ozawa et al. |
| 2014/0162901 A1 | 6/2014 | Bahrami et al. |
| 2014/0170299 A1 | 6/2014 | Gill |
| 2014/0228950 A1 | 8/2014 | Whitcup et al. |
| 2014/0228971 A1 | 8/2014 | Kim |
| 2014/0249504 A1 | 9/2014 | Franklin et al. |
| 2014/0257190 A1 | 9/2014 | Yue et al. |
| 2014/0309590 A1 | 10/2014 | Bahrami et al. |
| 2014/0343481 A1 | 11/2014 | Ignon |
| 2014/0350514 A1 | 11/2014 | Levin |
| 2014/0350516 A1 | 11/2014 | Schwab |
| 2014/0350517 A1 | 11/2014 | Dominguez |
| 2014/0350518 A1 | 11/2014 | Franklin et al. |
| 2014/0350536 A1 | 11/2014 | Allison |
| 2015/0025459 A1 | 1/2015 | Kimmell |
| 2015/0025563 A1 | 1/2015 | Mosharrafa et al. |
| 2015/0119875 A1 | 4/2015 | Fischell et al. |
| 2015/0126929 A1 | 5/2015 | Franklin et al. |
| 2015/0141956 A1 | 5/2015 | Hoffman et al. |
| 2015/0157809 A1 | 6/2015 | Park et al. |
| 2015/0209265 A1 | 7/2015 | Horne |
| 2015/0343147 A1 | 12/2015 | Franklin et al. |
| 2016/0007990 A1 | 1/2016 | Solish et al. |
| 2016/0058488 A1 | 3/2016 | Fourkas |
| 2016/0095984 A1 | 4/2016 | Franklin et al. |
| 2016/0114144 A1 | 4/2016 | Sumida |
| 2016/0144125 A1 | 5/2016 | Franklin |
| 2016/0207253 A9 | 7/2016 | Down et al. |
| 2016/0213854 A1 | 7/2016 | Schwab et al. |
| 2016/0263358 A1 | 9/2016 | Unger |
| 2016/0303314 A1 | 10/2016 | Momose |
| 2017/0080154 A1 | 3/2017 | Mudd et al. |
| 2017/0290987 A1 | 10/2017 | Mandaroux et al. |

FOREIGN PATENT DOCUMENTS

| | | |
|---|---|---|
| EP | 0362484 | 4/1990 |
| EP | 0205915 | 7/1990 |
| EP | 0167662 | 12/1990 |
| EP | 0648474 | 4/1995 |
| EP | 0809968 | 12/1997 |
| EP | 1051988 | 11/2000 |
| EP | 1486218 | 12/2004 |
| EP | 1395320 | 6/2006 |
| EP | 1859827 | 11/2007 |
| EP | 1923086 | 5/2008 |
| EP | 2189173 | 5/2010 |
| EP | 2335755 | 6/2011 |
| EP | 2422832 | 2/2012 |
| EP | 2103262 | 2/2013 |
| EP | 2184016 | 4/2013 |
| EP | 2671516 | 12/2013 |
| FR | 53011 | 9/1945 |
| FR | 2622457 | 5/1989 |
| FR | 2857654 | 1/2005 |
| GB | 2336783 | 5/2003 |
| IN | 209387 | 9/2007 |
| KR | 20120007473 | 1/2012 |
| KR | 101246570 | 3/2013 |
| KR | 20130036921 | 4/2013 |
| KR | 20130130436 | 12/2013 |
| KR | 20130132196 | 12/2013 |
| KR | 20140029007 | 3/2014 |
| RU | 2286803 | 11/2006 |
| WO | WO 90/001349 | 2/1990 |
| WO | WO 92/013579 | 8/1992 |
| WO | WO 94/012228 | 6/1994 |
| WO | WO 96/025965 | 8/1996 |
| WO | WO 97/028840 | 8/1997 |
| WO | WO 99/048601 | 9/1999 |
| WO | WO 01/00190 | 1/2001 |
| WO | WO 02/055135 | 7/2002 |
| WO | WO 2004/022603 | 3/2004 |
| WO | WO 2005/095225 | 10/2005 |
| WO | WO 2006/065837 | 6/2006 |
| WO | WO 2008/086479 | 8/2006 |
| WO | WO 2006/118804 | 11/2006 |
| WO | WO 2006/133111 | 12/2006 |
| WO | WO 2007/092929 | 8/2007 |
| WO | WO 2008/019265 | 2/2008 |
| WO | WO 2008/053481 | 5/2008 |
| WO | WO 2008/072229 | 6/2008 |
| WO | WO 2008/079824 | 7/2008 |
| WO | WO 2008/148071 | 12/2008 |
| WO | WO 2009/003135 | 12/2008 |
| WO | WO 2009/035680 | 3/2009 |
| WO | WO 2009/091099 | 7/2009 |
| WO | WO 2009/098666 | 8/2009 |
| WO | WO 2009/158145 | 12/2009 |
| WO | WO 2010/028025 | 3/2010 |
| WO | WO 2011/016785 | 2/2011 |
| WO | WO 2011/073796 | 6/2011 |
| WO | WO 2011/075731 | 6/2011 |
| WO | WO 2011/109129 | 9/2011 |
| WO | WO 2011/109130 | 9/2011 |
| WO | WO 2012/054301 | 4/2012 |
| WO | WO 2012/054311 | 4/2012 |
| WO | WO 2012/127856 | 9/2012 |
| WO | WO 2012/172424 | 12/2012 |
| WO | WO 2013/005881 | 1/2013 |
| WO | WO 2013/054165 | 4/2013 |
| WO | WO 2013/055832 | 4/2013 |
| WO | WO 2013/082112 | 6/2013 |
| WO | WO 2013/106857 | 8/2013 |

(56) References Cited

FOREIGN PATENT DOCUMENTS

| WO | WO 2014/026044 | 2/2014 |
|---|---|---|
| WO | WO 2014/034032 | 3/2014 |
| WO | WO 2012/174464 | 5/2014 |
| WO | WO 2014/064536 | 5/2014 |
| WO | WO 2014/189161 | 11/2014 |
| WO | WO 2015/007243 | 1/2015 |
| WO | WO 2015/020982 | 2/2015 |
| WO | WO 2013/065235 | 4/2015 |
| WO | WO 2015/064031 | 5/2015 |
| WO | WO 2015/105269 | 7/2015 |
| WO | WO 2015/127339 | 8/2015 |
| WO | WO 2015/149031 | 10/2015 |
| WO | WO 2016/008845 | 1/2016 |
| WO | WO 2016/022865 | 2/2016 |
| WO | WO 2016/033584 | 3/2016 |
| WO | WO 2016/033586 | 3/2016 |

OTHER PUBLICATIONS

Davidenko et al., "Collagen-hyaluronic acid scaffolds for adipose tissue engineering", ACTA Biomaterialia, vol. 6, No. 10, Oct. 1, 2010, pp. 3957-3968.
Galderma, "New Restylane Skinboosters SmartClick delivery system wins prestigious Red Dot design award," Jul. 4, 2014, retrieved from http://www.galderma.com/News/articleType/ArticleView/articleId/64/New-Restylane-Skinboosters-SmartClick-delivery-system-wins-prestigious-Red-Dot-design-award.
Galderma, "Restylane Smart Click System Injection Device," Mar. 2015, retrieved from http://www.red-dot-21.com/products/restylane-smart-click-system-injection-device-22169.
Hamza et al., "A new external filling device in tissue expansion," Plastic and Reconstructive Surgery, March 1998, vol. 101, No. 3, pp. 813-815
Indian Patent Application No. 190/CHE/2002, filed Mar. 20, 2002, entitled A Subcutaneous Tissue Expander, 5 pages.
Indian Patent Application No. IN2012KO01267 for Tissue Expander, Feb. 8, 2017, 7 pages.
International Search Report from PCT/US2016/021838, dated May 17, 2016, 3 pages.
International Search Report and Written Opinion from PCT/US2009/045831, dated Feb. 24, 2010, 14 pages.
International Search Report and Written Opinion from PCT/US2014/039265, dated Nov. 18, 2014, 18 pages.
International Search Report and Written Opinion from PCT/US2014/039266, dated Aug. 26, 2014, 13 pages.
Park et al., "Biological characterization of EDC-crosslinked collagen-hyaluronic acid matrix in dermal tissue restoration", Biomaterials, Elsevier Science Publishers BV, vol. 24, No. 9, Apr. 1, 2003, pp. 1631-1641.
Prime Journal, "Galderma to launch two new syringes at AMWC 2014," Mar. 2014, 4 pages.
Turtlepin, "The Painless Direct Dermal Injector" Product Information, JM Biotech Co Ltd, 2013, 18 pages.
Wang et al., "In vivo stimulation of de novo collagen production caused by cross-linked hyaluronic acid dermal filler injections in photodamaged human skin.", Archives of Dermatology, American Medical Association, US, vol. 143, No. 2, Feb. 1, 2007, pp. 155-163.

\* cited by examiner

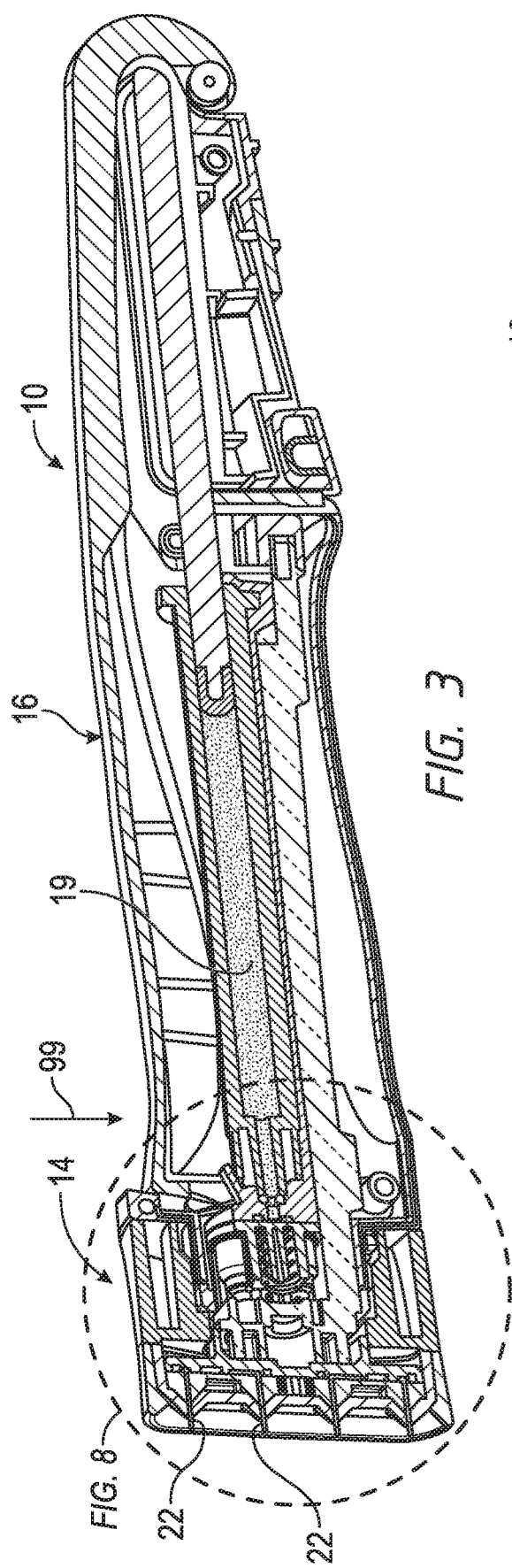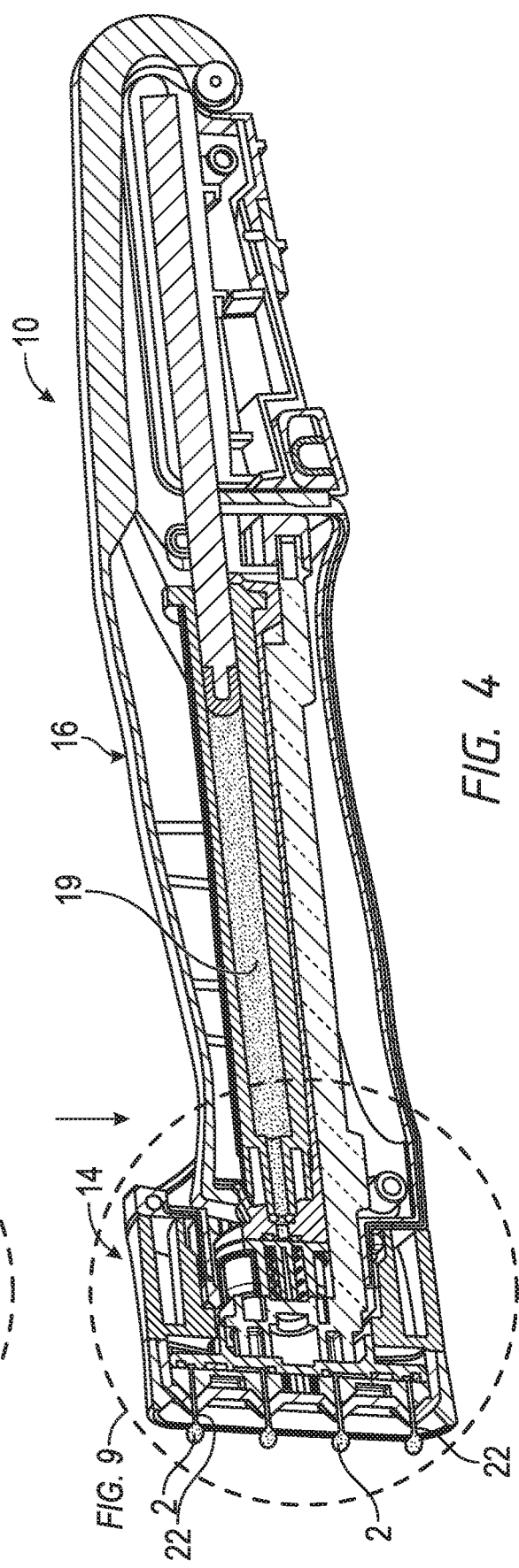

DEVICES FOR INJECTION AND DOSING

This application is a continuation of U.S. patent application Ser. No. 14/852,903, filed on Sep. 14, 2015, which claims the benefit of U.S. Patent Application Ser. No. 62/058,587 filed on Oct. 1, 2014, and claims the benefit of U.S. Patent Application Ser. No. 62/187,077, filed on Jun. 30, 2015, the entire contents of each of these applications being incorporated herein by this specific reference.

The present invention generally relates to mechanisms for injection and dosing, and more specifically relates to devices for providing minute doses of dermal filler composition superficially into skin.

BACKGROUND

Aesthetic dermal filler procedures have become increasing popular in recent years, as they have proven to be quite effective in improving the appearance of the face, for example, in reducing the signs of aging by smoothing wrinkles and folds, such as the nasolabial folds, and plumping the midface. Some of the more popular dermal fillers are soft, colorless gel compositions made of hyaluronic acid. Hyaluronic acid (HA) is a long chain polymer, more specifically, a polysaccharide, which occurs naturally in body tissues. When chemically crosslinked, hyaluronic acid makes an excellent, long lasting, dermal filler material. Dermal filler procedures are quite minimally invasive, and the results are nearly immediate. Further, hyaluronic acid naturally degrades in the body tissues, and thus the fillers are temporary, for example, lasting several months to a year or more. Further, results of hyaluronic acid based dermal filler procedures can be reversed using hyaluronidase.

Conventional dermal filler procedures are generally performed by injection of the composition into or below the skin using a standard syringe and a fine gauge needle. A typical dermal filler patient may undergo from about 5 to about 10 injections in a single procedure, with injection points across various regions of the face. While the goal may be to improve the appearance of the entire face, a skilled aesthetic physician generally aims to correct one or more specific regions of the face, for example, regions that lack volume such as the lips or the cheeks, or regions that present specific wrinkles, such as deep nasolabial folds, with specific input from the patient regarding areas he or she finds detracting to his or her appearance.

It has been discovered that improvement of facial appearance can also be accomplished by introducing minute amounts of compositions into skin at a very superficial depth, and across wide regions of the skin, rather than focusing on specific wrinkles or specific areas of the face that lack volume.

SUMMARY

The present invention is generally directed to a device that can be used to deliver a composition into skin, for example, in a way that is effective to treat or improve the skin surface. The device is structured for treating or improving skin by delivering a composition, for example a gel, for example, a dermal filler gel, into skin, at a relatively shallow depth, to improve the appearance of the skin, and perhaps improve overall skin health and quality. The device advantageously facilitates treatment of a large surface area of skin, such as the entire face, neck and/or décolletage, or significant regions thereof. The device allows for controlled depth of injection, especially for superficial intradermal delivery of compositions, for example, dermal filler gels or other compositions effective to enhance the health or appearance of skin. The injection may be between about 0.5 mm about 3 mm for intradermal injection, or deeper for subdermal injection.

For example, the device is more efficient at delivering doses of a hyaluronic acid based dermal filler to a large surface area of skin than is currently possible with a standard needle and syringe.

In some embodiments, a dermal filler injection device is provided which generally comprises a handpiece including a housing having an interior space for containing a cartridge and a trigger coupled to the housing. The device further includes a head in communication with the interior space. In some embodiments, the head is removable with respect to the handpiece. In some embodiments, the device includes at least one retractable needle and at least one dosing chamber coupled thereto. Operation of the trigger causes the needle to be moved from a retracted position to an extended position and a dose of a composition to be delivered from the needle tip.

In some embodiments, the at least one needle comprises a plurality of needles, with each one of the needles coupled to a corresponding one of the dosing chambers. In this embodiment, the device may be structured such that operation of the trigger initially causes the plurality of needles to be moved from a retracted position to an extended position and subsequently causes a dose of fluid contained in the corresponding dosing chambers to be ejected from the needles, for example, substantially simultaneously, when the needles are in the extended position. The device may be further structured to cause retraction of the needles after the dosing. In some embodiments the device includes a mechanism capable of filling each dosing chamber between subsequent injections.

The plurality of needles may comprise linearly arranged needles, for example, at least three, for example, about four, or more linearly arranged needles. In some embodiments, the needles are arranged in an array. For example, the needles may be arranged in a two by two array, a two by three array, a four by four array, a six by six array, a two by four array, or any other suitable configuration.

In one embodiment, the head of the device may include a plurality of conical or tapered projections, each needle having a tip protruding from an individual conical or tapered projection. For example, each conical or tapered projection is spaced apart from each other conical or tapered projections so as to effect a preloading of skin when the head is applied to skin, to facilitate penetration of the needle tips into the skin.

In one aspect, a method for treating skin is provided, wherein the method generally comprises placing a distal end of a handheld device into direct contact with skin to be treated; causing the device to inject a dose of a composition into the skin through a plurality of needles, substantially simultaneously; moving the distal end of the device onto another portion of the skin while maintaining the direct contact with the skin; and, after the step of moving, causing the device to inject another dose of the composition into another portion of the skin. In another aspect of the invention, the needles are in a retracted position during the moving step. The needles are in an extended position during the dosing or delivery of the composition into the skin.

BRIEF DESCRIPTION OF THE DRAWINGS

The various aspects and advantages of the different embodiments may be better understood by referring to the following Detailed Description and accompanying Drawings of which:

FIG. 3 shows a cross-sectional view of the device shown in FIG. 1, the device in an initial stage of trigger activation;

FIG. 4 shows a cross-sectional view of the device shown in FIG. 1, the device in a stage of full trigger activation;

DETAILED DESCRIPTION

Figure 1:
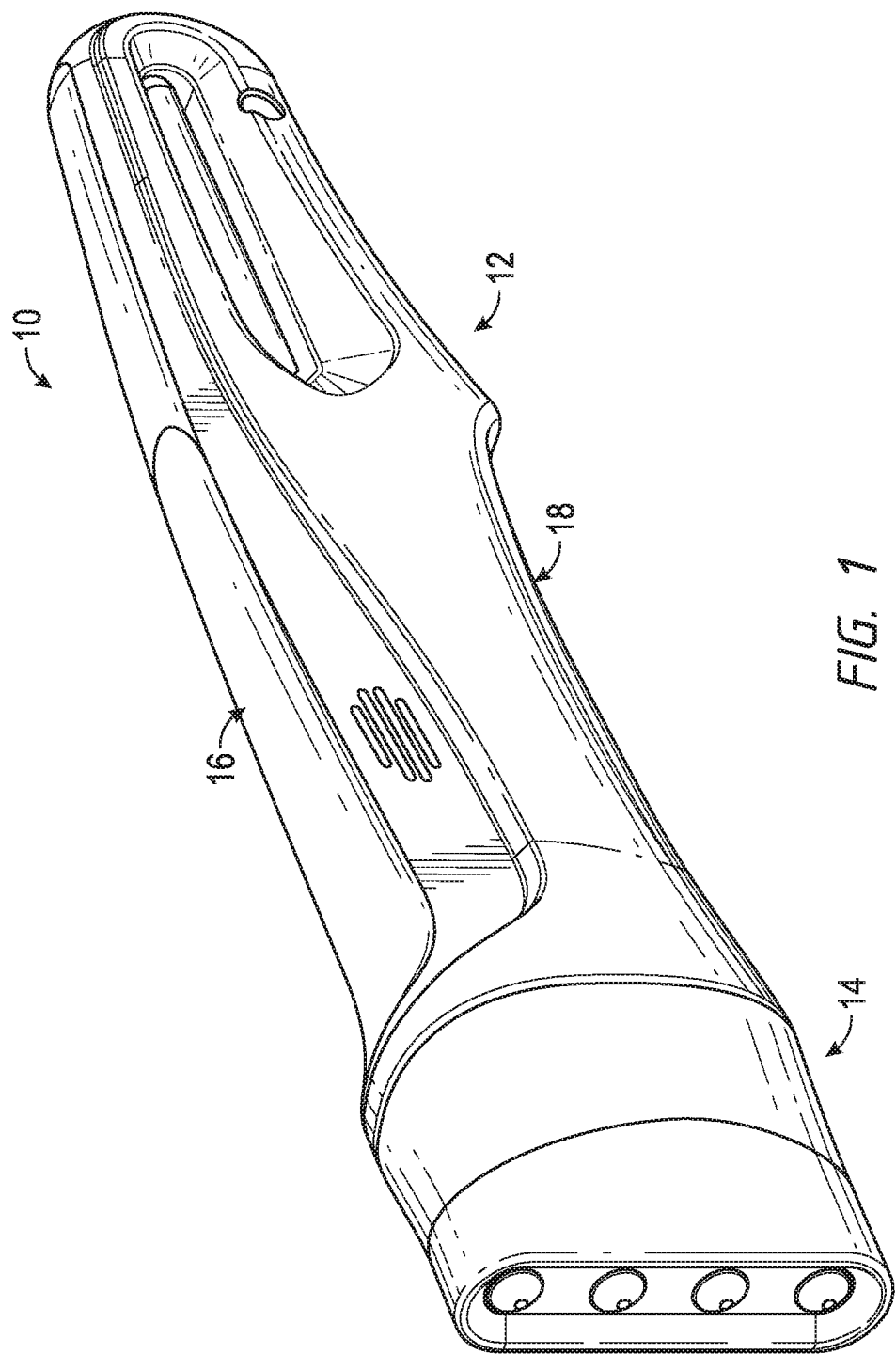
FIG. 1 shows a perspective view of a device in accordance with an embodiment of the invention.

A device 10 in accordance with an exemplary embodiment of the invention is shown in FIG. 1. Device 10 is configured and shaped to be held and operated by a single hand of a user, for example an aesthetic physician. Device may be used to deliver micro-depot injections of composition into skin, with the aim of improving the appearance of skin, for example, reducing the appearance of fine lines or superficial skin depressions, thereby improving skin texture. Depending on the composition being delivered, device 10 may also be effective for use in improving or increasing skin elasticity and hydration.

Device 10 generally comprises a handpiece 12, and a head 14 coupled thereto. The handpiece 12 includes a main housing 18, and a trigger 16 coupled to the main housing 18.

Figure 2:
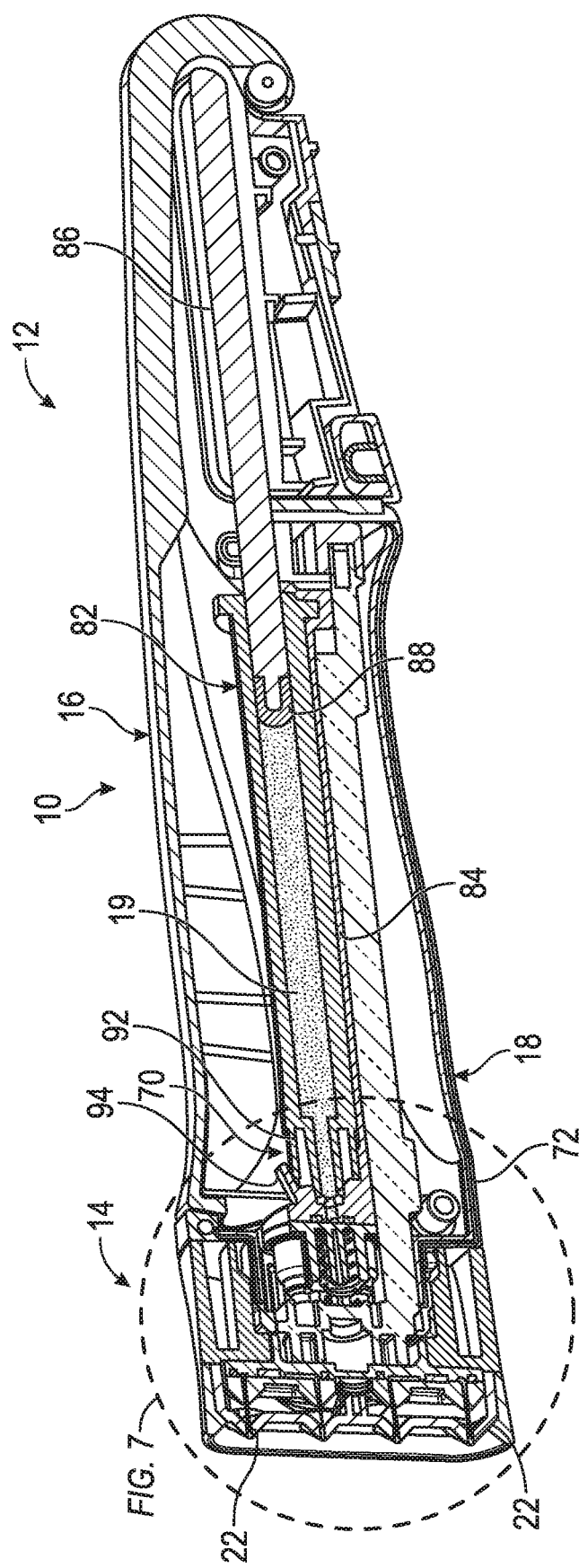
FIG. 2 shows a cross-sectional view of the device shown in FIG. 1, the device in a neutral position.

As shown in FIGS. 2-4, device 10 is shown in the several operational stages that occur during operation of the device 10 when used to deliver multiple, shallow, doses of a composition 19 into skin.

Turning now to FIG. 2, the device 10 is shown, in cross-sectional view, in a neutral position, for example, a position of which the device 10 is not yet actuated, and is ready to be used to introduce the composition 19, for example, a dermal filler, for example, a crosslinked and/or uncrosslinked hyaluronic acid-based dermal filler, or other beneficial composition.

When the device 10 is in the neutral position, needles 22 of the device 10 are positioned in a retracted position within the head 14. At this stage, handpiece 12 is comfortably grasped by the user, and is placed into contact with a region of a patient's skin (not shown) to be treated, with the head 14 of the device 10 touching the skin.

FIG. 3 shows the device 10 during an initial stage of the trigger 16 being manually pressed, for example by a thumb or index finger of the user, in which the needles 22 are caused to be moved to an extended position. As the needles 22 extend, they are caused to puncture the surface of the skin in contact with the head 14.

Turning to FIG. 4, as the user continues to press trigger 16, multiple small, shallow doses 2, aliquots, or micro depots of the composition, are delivered from the extended needles 22 and into the skin.

Needles may be spaced apart from one another any suitable distance. In the embodiment shown, adjacent needles are spaced apart about 10 mm. In other embodiments, the spacing between adjacent needles may be, for example, less than 10 mm, for example, about 3 mm, about 5 mm, about 7 mm. In yet other embodiments, the needles are spaced apart more than 10 mm, for example, about 12 mm, about 14 mm, about 16 mm, or about 20 mm, or more. In yet other embodiments, spacing between adjacent needles is about 1 mm to about 20 mm, for example, about 3 mm to about 14 mm, for example, about 5 mm to about 12 mm, for example, about 7 mm to about 10 mm.

Figure 5:
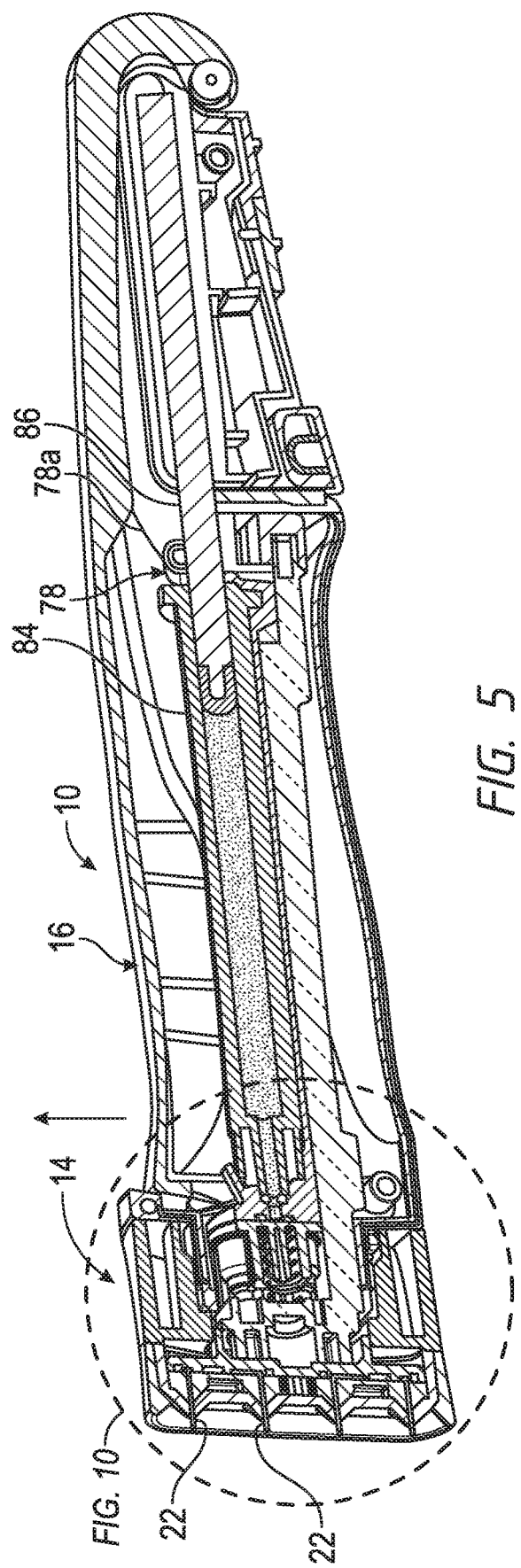
FIG. 5 shows a cross-sectional view of the device shown in FIG. 1, the device in an initial stage of trigger retraction.
Figure 6:
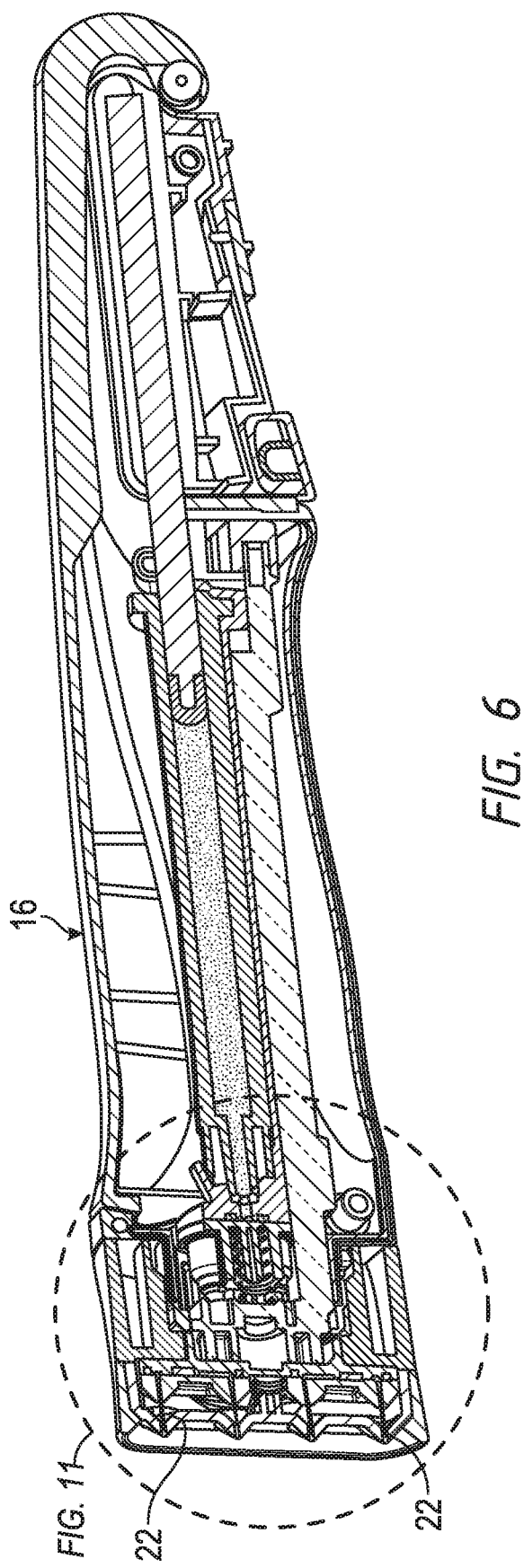
FIG. 6 shows a cross-sectional view of the device shown in FIG. 1, the device in a neutral position.

As illustrated in FIG. 5, as the user initially releases pressure on the trigger 16, the needles 22 remain for a moment in the extended position, while the dosing of composition from the device 10 is stopped. FIG. 6 shows that upon completion of the release of the trigger 16, the needles 22 have moved back into the retracted position, and the device 10 once again in the neutral position, is ready to be actuated for the next dose.

The operational mechanism of device 10 may be more clearly understood with reference to the magnified views of FIGS. 7-11.

Figure 7:
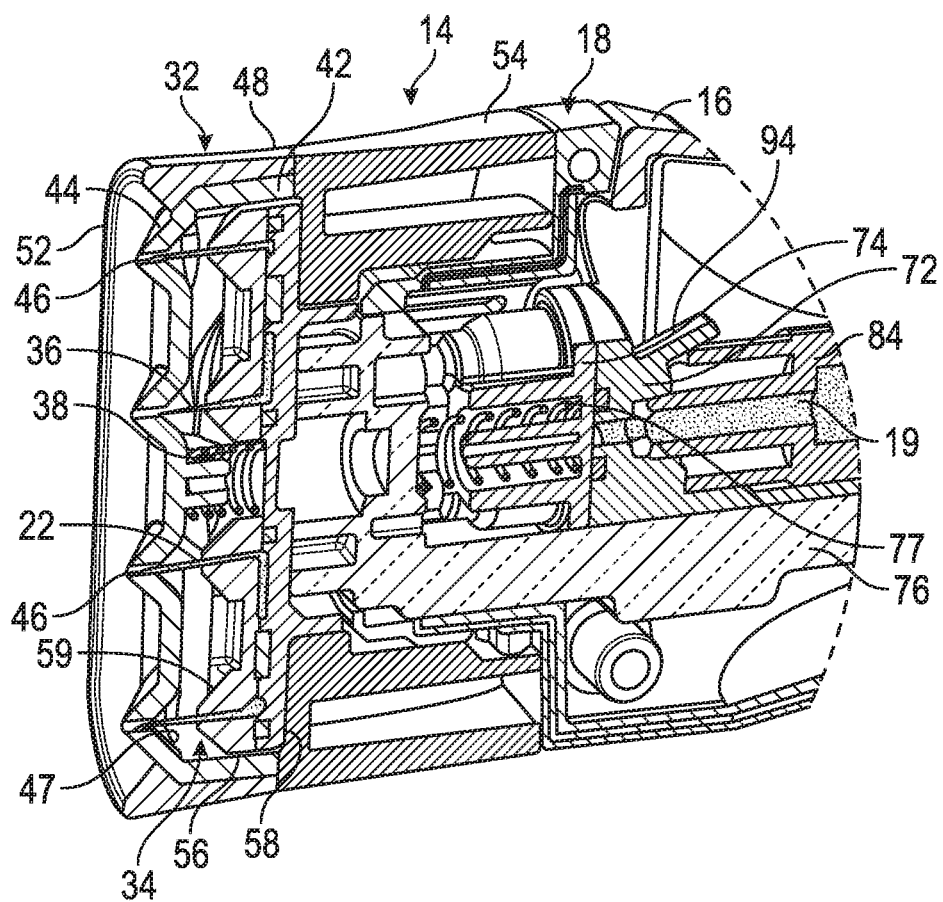
FIG. 7 shows a magnified view of a distal end of the device taken from FIG. 2.

Turning now to FIG. 7, head 14 comprises a needle array housing assembly 32, and a needle hub 34 disposed within the needle array housing assembly 32. A plurality of needles 22, for example, four needles 22, are secured in the needle hub 34. A needle assembly spring 38 is seated between the needle array housing assembly 32 and the needle hub 34.

Figure 17:
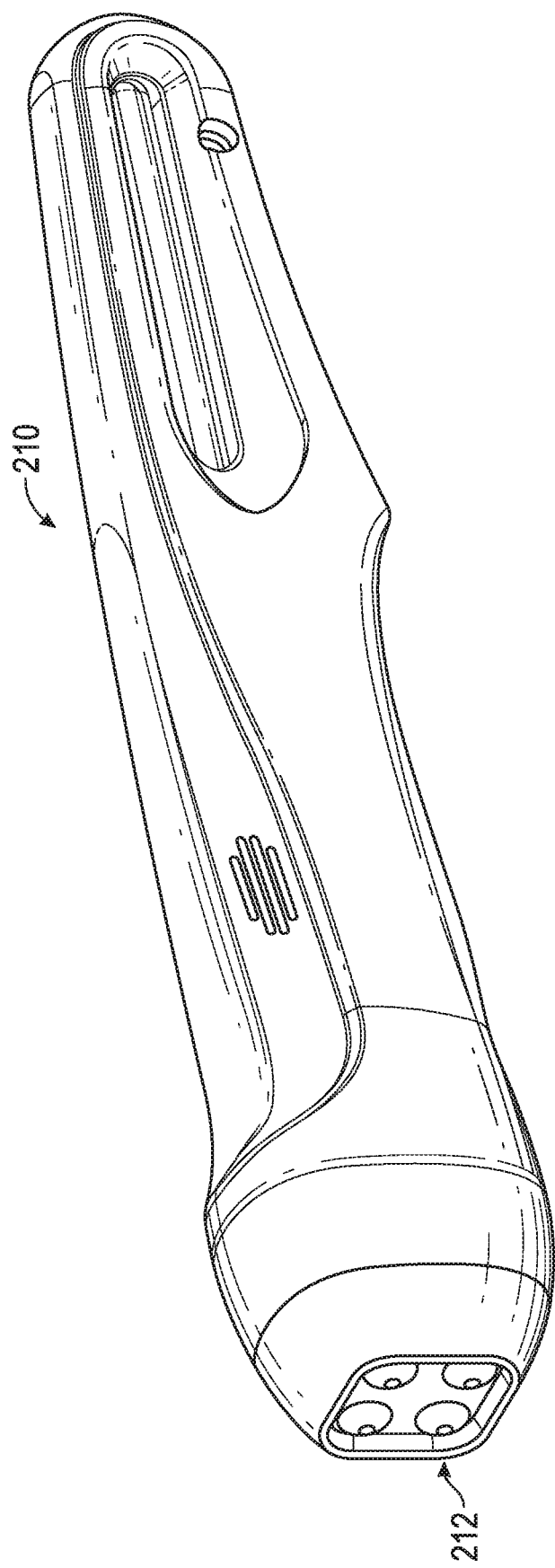
FIG. 17 shows an alternative embodiment of the device of the invention.

Needles 22 may be arranged linearly, as shown, for example, arranged in a single row of three or more, for example, four to about 20 or more, needles. The exemplary embodiment shown comprises a 1×4 needle array. Alternative devices of the invention including different needle array arrangements include other devices having other arrays, such as, for example but certainly not limited to, a 1×3 array, a 3×3 array, a 2×3 array, or a 4×4 needle array 212, such as device 210 shown in FIG. 17. Any other suitable needle array (e.g. a×b, wherein a is at least one and up to 20, or more, and b is at least one and up to 20, or more), may be provided within the scope of the invention.

Needle array housing assembly 32 comprises a needle portion 42 having distal projecting regions 44, for example, four projecting regions 44, each distal projecting region 44 having an aperture 46 for receiving one of the needles 22, and a recess 47. Needle array housing assembly 32 further comprises a contact portion 48 having a distal surface 52 generally circumscribing the distal projecting regions 44. Needle array housing assembly 32 further comprises a base portion 54, which may abut against main housing 18 of handpiece 12.

In some embodiments, the device 10 is structured to facilitate injection. For example, the projecting regions 44 are in the form of conical or tapered projections, as shown, with each needle 22 protruding from an individual conical or tapered projection 44. In some embodiments, each conical or tapered projection 44 is spaced apart from each other conical or tapered projections so as to effect a preloading of skin when the head 14 is applied to skin during treatment. By preloading of the skin, the conical or tapered portions 44 facilitate penetration of the needle tips into the skin.

Needle hub 34 comprises a first portion 56 and a second portion 58 rigidly secured together and holding the needles 22. First portion 56 includes hub projecting regions 59, for example, four hub projecting regions 59. Each hub projecting region 59 is aligned with a recess 47 of a corresponding distal projecting region 44 of the needle array housing assembly 32, as shown.

Briefly turning back to FIG. 2, the handpiece 12 includes an internal assembly 70, which, upon manual activation of trigger 16, is urged forward, i.e. distally, within the handpiece main housing 18, to cause dispensing of an accurate, shallow dose of the composition 19 into skin by way of the needles 22, as will be described in greater detail hereinafter.

Figure 12:
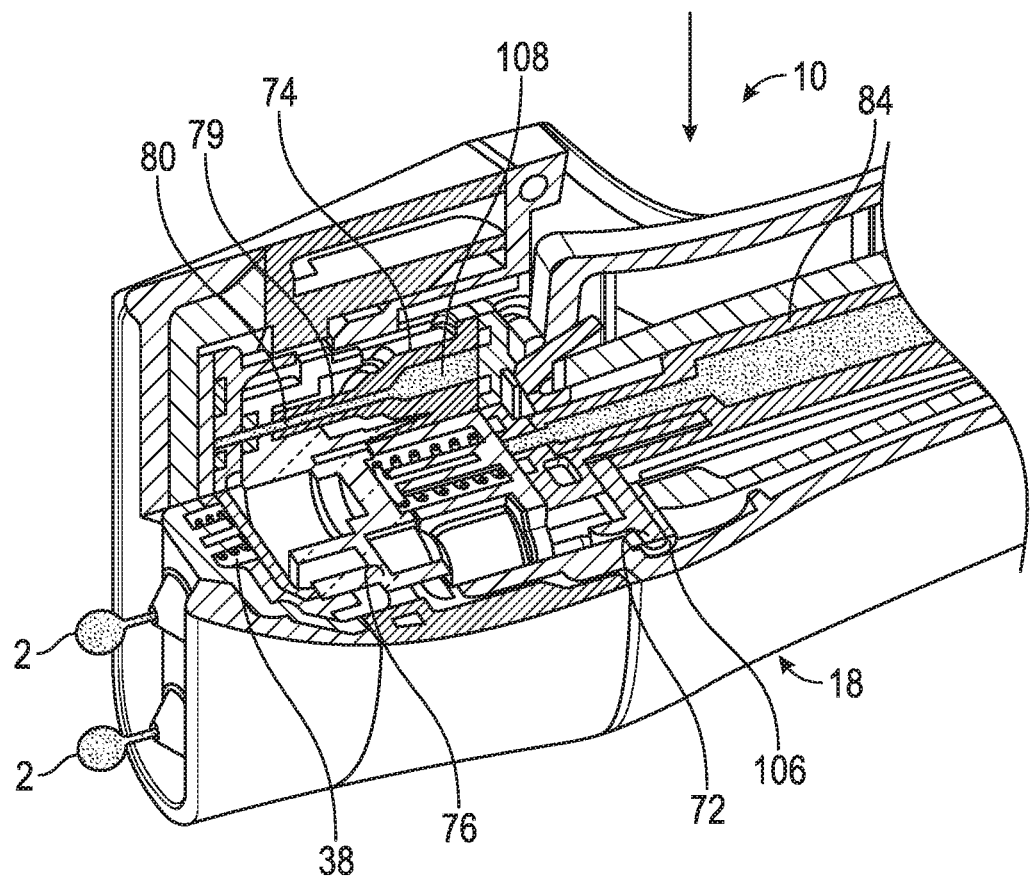
FIG. 12 shows a cutaway view of the distal end of the device during injection.
Figure 16:
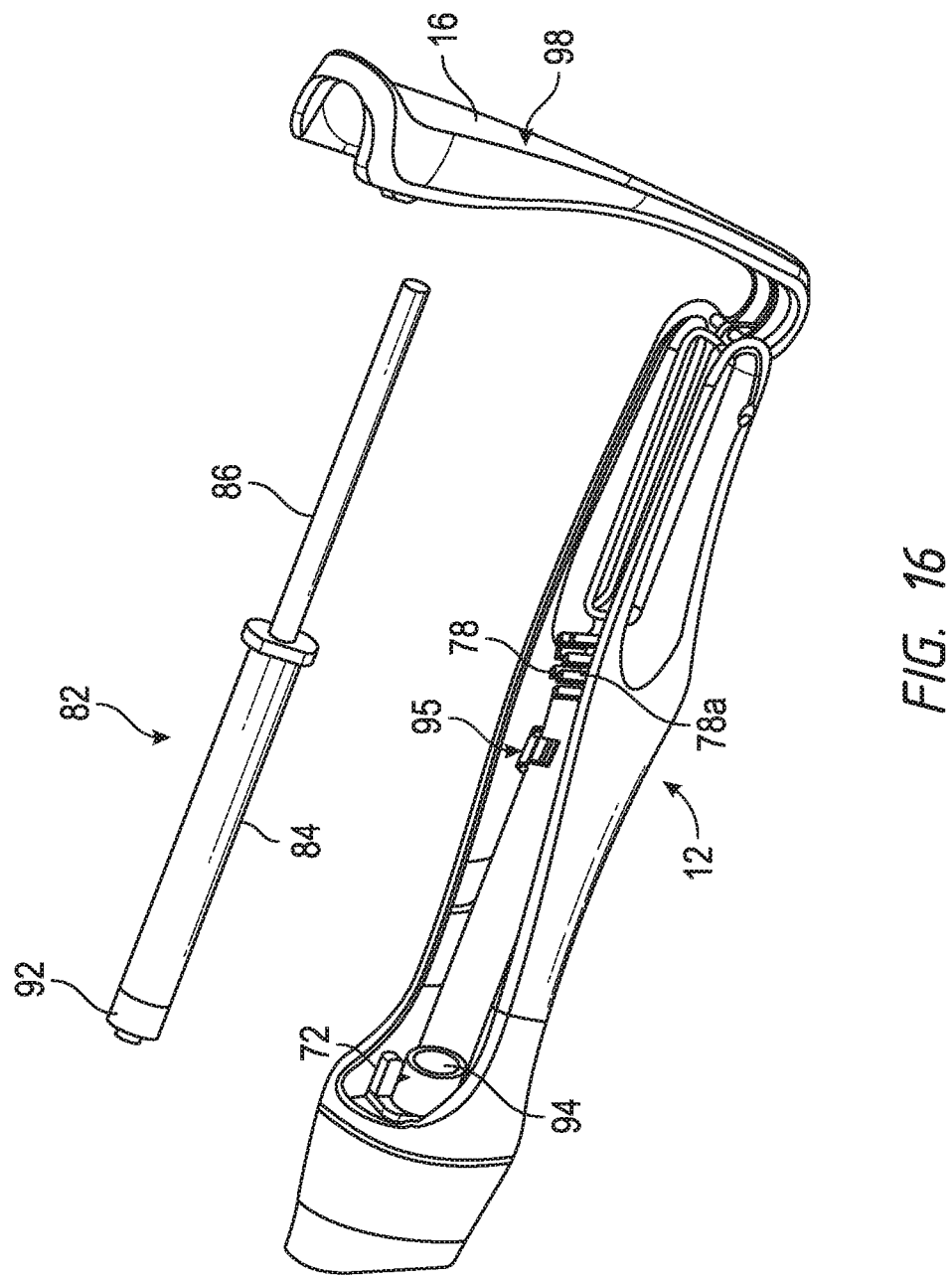
FIG. 16 shows the device of FIG. 1 with a removable cartridge.

Referring back to FIG. 7, internal assembly 70 generally comprises a distribution manifold 72, a dosing manifold 74, a dosing block 76, a dosing spring 77, and a one-way mechanism 78 (see briefly FIG. 5 or FIG. 16). Distribution manifold 72 and dosing manifold 74 are rigidly connected together and sealed. Referring briefly to FIG. 12, dosing manifold 74 includes individual plungers 79 which correlate with individual dosing chambers 80 in the dosing block 76. Although they are not all visible in the Drawings, in this exemplary embodiment, there are four dosing chambers 80 and four corresponding dosing plungers 79, since the shown embodiment includes four needles 22.

Although the exemplary device 10 is a four needle embodiment, it should readily be appreciated that other embodiments of the device not shown may include any number of needles, for example, less than four, for example, two or three, or more than four, for example, five, ten, twenty or more, wherein the device is structured such that each needle has a corresponding dosing chamber and individual plunger, with the required modifications to the components of the invention, and all these embodiments are considered to fall within the scope of the invention.

As shown most clearly perhaps in FIG. 2, the handpiece 12 includes an interior space, for example, defined by the handpiece main housing 18, for receiving a cartridge assembly 82. The device 10 is structured such that the cartridge assembly 82 is removable from the handpiece main housing 18 and replaceable. Cartridge assembly 82 comprises a cartridge 84 containing the composition 19 to be injected, and a cartridge plunger 86 slidable within the cartridge 84 and including plunger head 88 in contact with composition 19. Cartridge 82 includes cartridge distal portion 92.

Figure 5A:
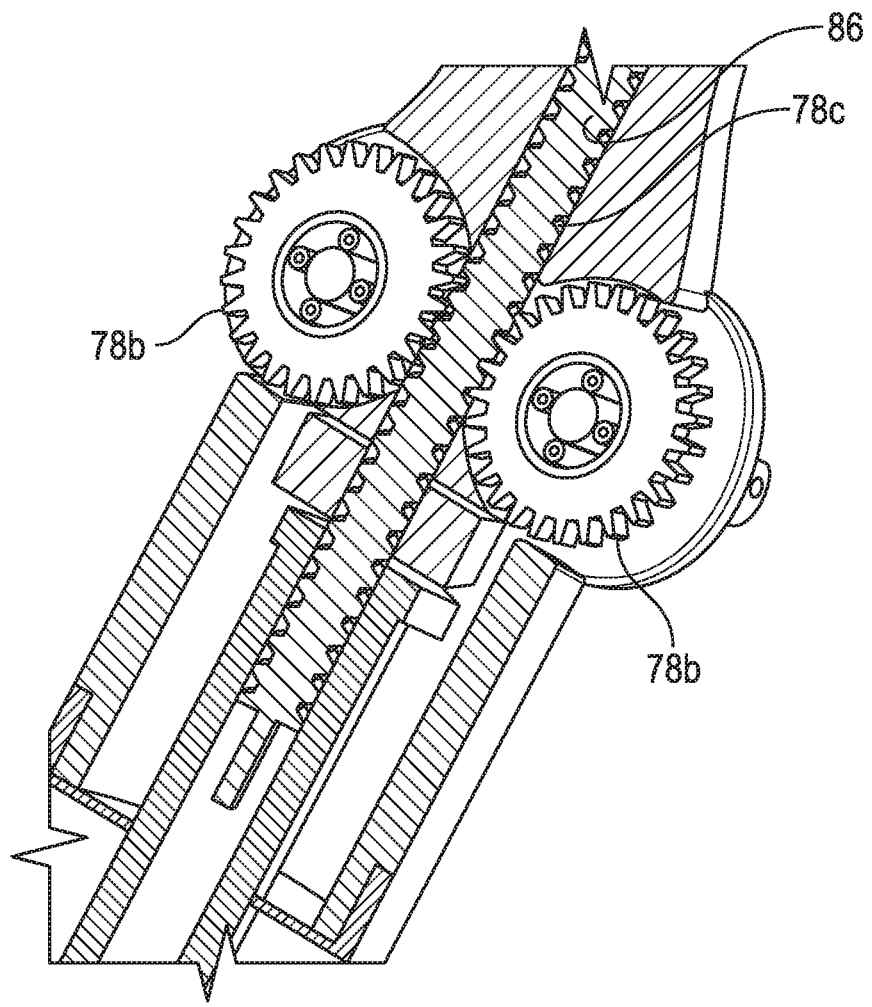
FIG. 5A shows an alternative one-way mechanism useful in some embodiments of the invention.

As shown in FIG. 5, the one-way mechanism 78 may be in the form of any mechanical structure that allows cartridge plunger 86 to move only in the distal direction during operation of the device 10. For example, one-way mechanism 78 may be in the form of elements 78a, such as leaves, for example, rigid or flexible leaves, that taper inwardly against and/or otherwise engage the cartridge plunger 86 and prevent the linear motion of that cartridge plunger 86 in one of two directions, for example, prevent the movement of the plunger 86 in a reverse or proximal direction, while enabling the plunger 86 to move in a forward, or distal direction. Alternative mechanisms are also contemplated and considered to be within the scope of the invention. For example, the one-way mechanism may be in the form of gears 78b and teeth 78c on plunger, such as shown in simplified view in FIG. 5A, such that the cartridge plunger 86 can move forwardly, but not backward.

Referring back to FIG. 7, distribution manifold 72 includes flange structure 94 which is mateable with cartridge distal portion 92. Forward (distal) motion of the cartridge plunger 86 pushes composition contained in the cartridge 84 forward and toward distribution manifold where it is distributed among the dosing chambers 80, and eventually ejected from the needles 22.

The dosing chambers 80 may each be sized to contain a drop or an aliquot of composition to be injected. By way of example only, the dosing chamber 80 may be sized or structured to contain at least 2 μl and up to about 100 μl or 200 μl or greater of a composition. For example, in some embodiments, the dosing chamber 80 is sized and/or structured to contain between about 2 μl and about 100 μl of a composition, for example, between about 5 μl and about 50 μl, for example, between about 10 μl and about 40 μl of composition per dosing chamber 80. In some embodiments, each dosing chamber 80 is sized and/or structured to contain, for example, about 20 μl, about 40 μl, about 60 μl, about 80 μl, about 100 μl, or more of a composition.

Briefly referring to FIG. 16, cartridge assembly 82 may be removable from the handpiece 12, and replaceable. As shown, main housing 18 includes pivotable portion 98. Pivotable portion 98 may encompass the trigger 16. To replace the cartridge assembly 82, cartridge distal portion 92 snaps into flange structure 94 of distribution manifold 72, as well as retaining clips 95 of the distribution manifold 72, and cartridge plunger 86 is coupled to one-way mechanism 78. Once the cartridge assembly 82 is loaded into the handpiece 12, pivotable portion 98 is pivoted closed and the device 10 is in the neutral position (FIGS. 2 and 7) and is ready to use. In alternative embodiments, the cartridge assembly is refillable, but not readily removable by a user of the device.

Figure 8:
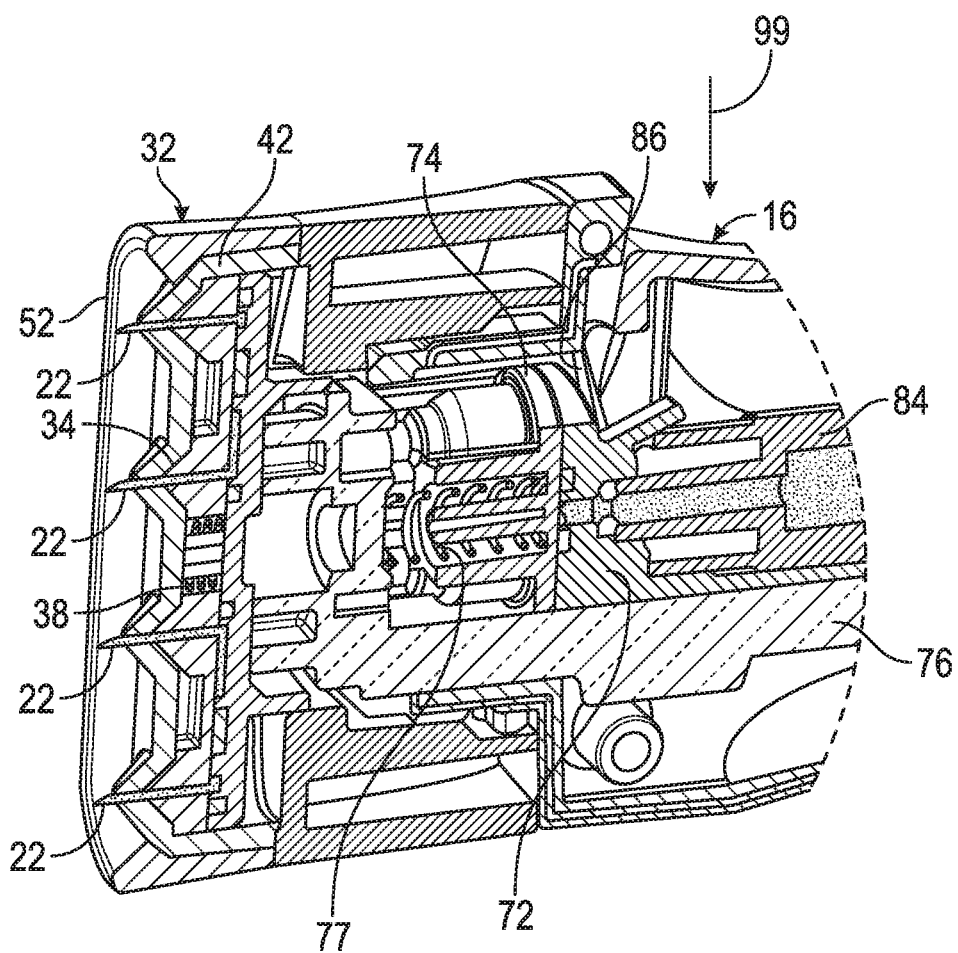
FIG. 8 shows a magnified view of the distal end of the device taken from FIG. 3.

Turning to FIG. 8, the user begins to press the trigger 16 in the direction indicated by arrow 99.

As the trigger 16 moves, a cam surface 96 on an internal portion of the trigger 16 presses on rollers 106 (see FIG. 12) which are attached to the distribution manifold 72. This action moves the distribution manifold 72, dosing manifold 74, dosing block 76, and one-way mechanism (not shown in FIG. 8), cartridge 84, cartridge plunger (not shown in FIG. 8), and needle hub 34 forward, compressing needle assembly spring 38. This causes the needles 22 to be extended relative to portion 42 of needle array housing assembly 32, and past the distal surface 52. In the shown embodiment, the needles extend approximately 0.5 mm to about 2.0 mm, or more specifically, about 1.5 mm. It can be appreciated that the needles may extend a distance less than 0.5 mm or greater than 2.0 mm, in accordance with different embodiments of the invention.

Figure 9:
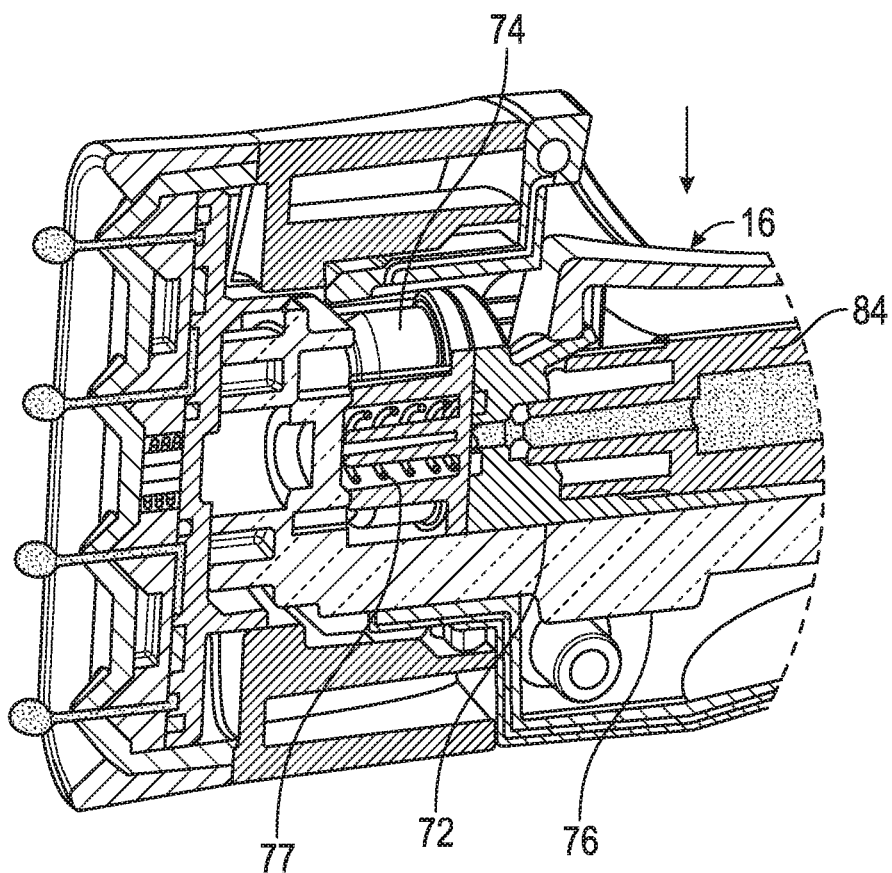
FIG. 9 shows a magnified view of the distal end of the device taken from FIG. 4.
Figure 10:
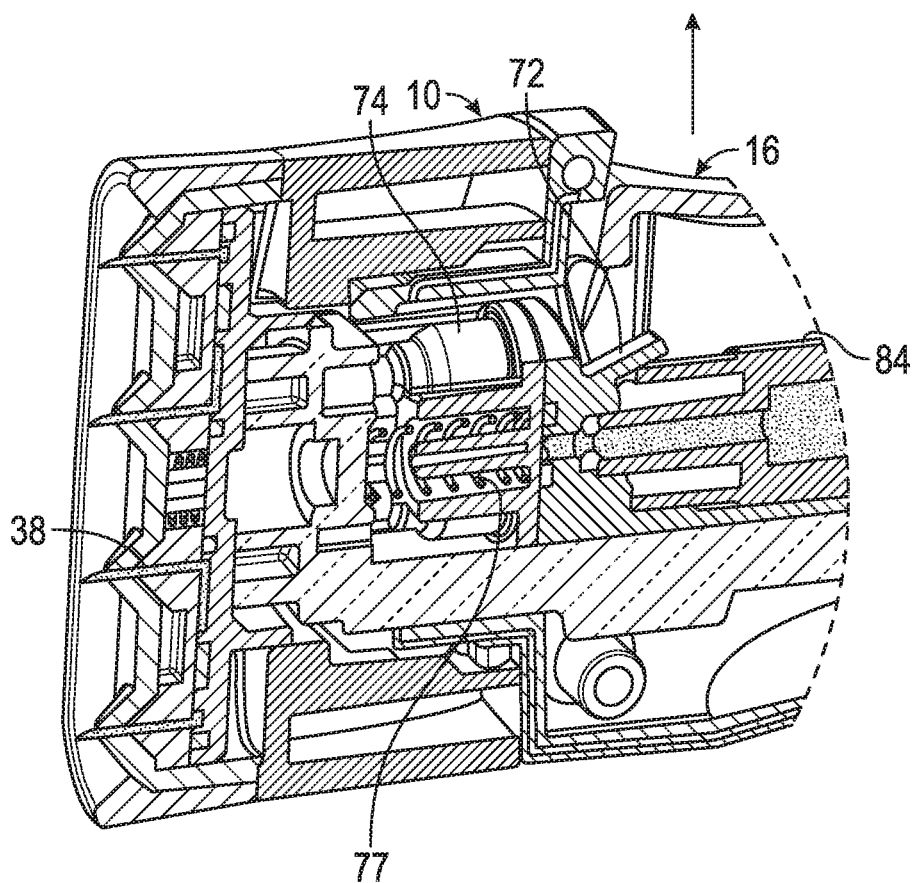
FIG. 10 shows a magnified view of the distal end of the device taken from FIG. 5.
Figure 11:
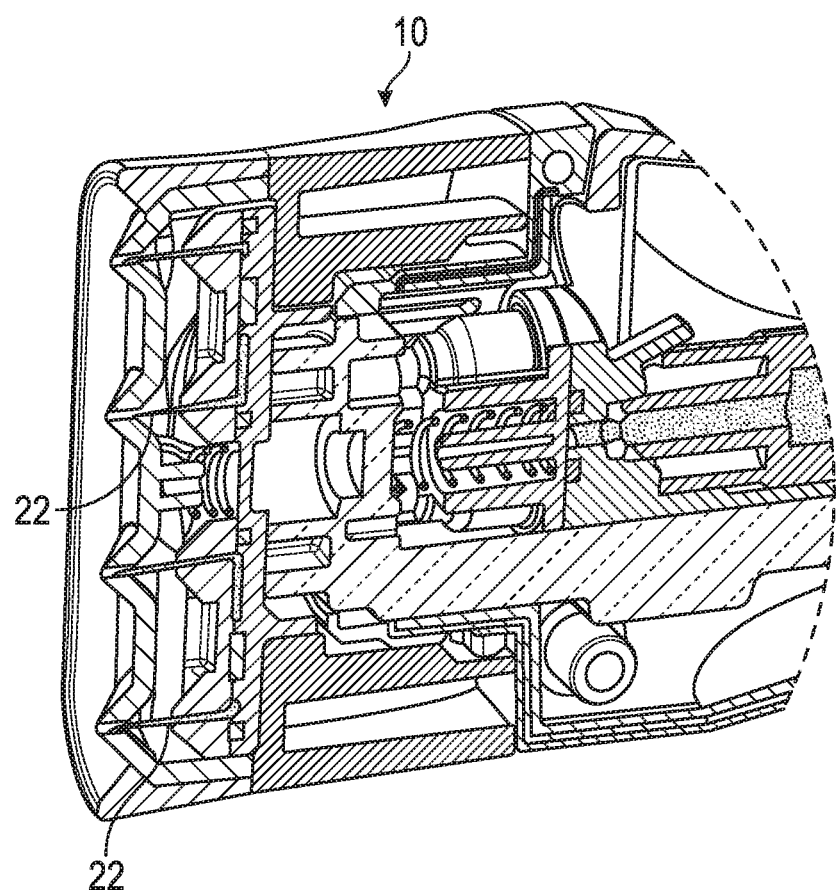
FIG. 11 shows a magnified view of the distal end of the device taken from FIG. 6.

Once the needle hub 34 has fully compressed the needle assembly spring 38, and has reached the limit of its travel, the needle hub 34 and dosing block 76 and one way mechanism stop moving, and the dosing spring 77 begins to compress. As shown in FIG. 9, as the dosing spring 77 compresses, the distribution manifold 72, dosing manifold 74, cartridge 84 and cartridge plunger (not visible in FIG. 9) continue to move forward (distally).

Turning briefly back to FIG. 12, the individual plungers 79 of the dosing manifold 74 deliver small doses 2 of the composition 19 through the needles 22 by compressing the dosing chambers 80 defined in the dosing block 76, which is not moving with respect to the housing 18. (Prior to this stage, the dosing block 76 was slidable with respect to housing 18). Check valves 108, closed during dosing, may be provided to prevent composition 19 from flowing back into the cartridge 84. When the trigger 16 is fully compressed (FIGS. 4, 9 and 12), the dose is fully delivered.

The present invention may further include a mechanism capable of filling each dosing chamber between subsequent injections. For example, turning to FIGS. 5 and 10, when the trigger 16 is released, the dosing spring 77 is the first to expand, which pushes the distribution manifold 72/dosing manifold 74 and cartridge 84 back (proximally), but the cartridge plunger 86 gets trapped in one-way mechanism 78 and cannot move back with the cartridge 84. The cartridge 84 moving back over the stationary cartridge plunger 86 causes liquid to flow from the cartridge 84 through the distribution manifold 72/dosing manifold 74 going through the check valves 108 (not visible in FIG. 10). In some embodiments, the needle diameter is small relative to other flow paths and acts as a shut off valve during the filling of the dosing chambers. so the injectable composition does not leak out the needles. Once full, the dosing spring 77 can no longer expand the assembly and now the whole internal assembly starts to move back under the force of the needle assembly spring 38. This retracts the needles 22 back into the device 10 (see FIG. 11) and it is now ready for another cycle.

Figure 13:
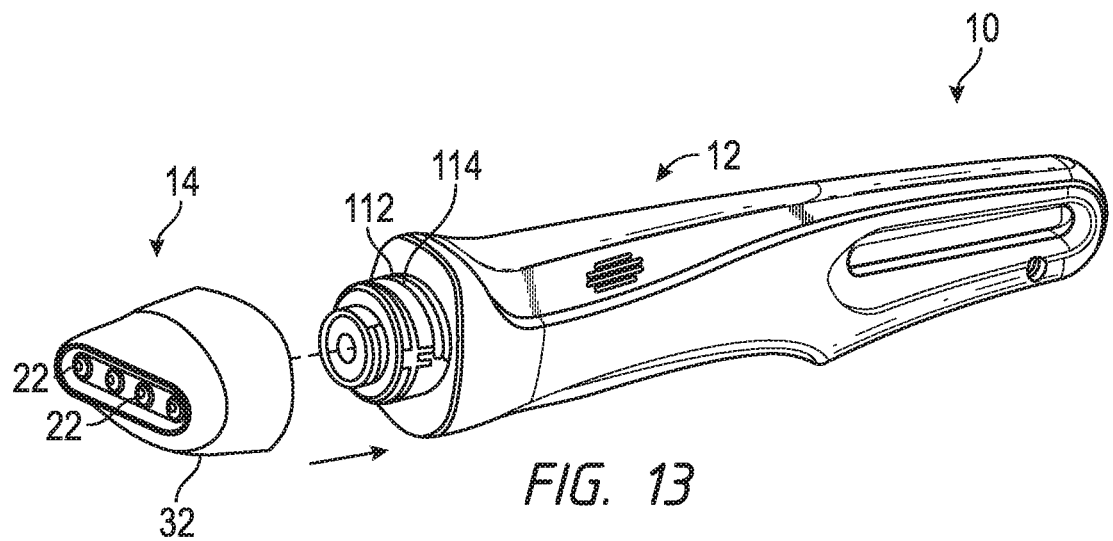
FIGS. 13-15 show perspective views of the device including a removable head feature.
Figure 14:
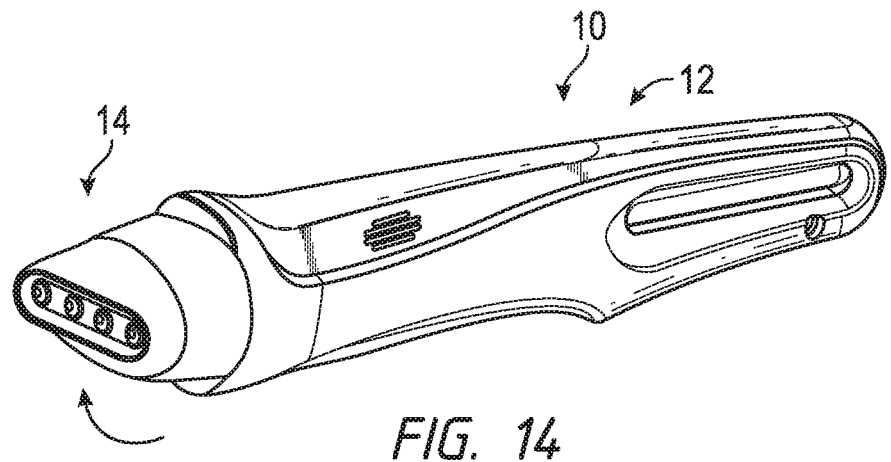
Figure 15:
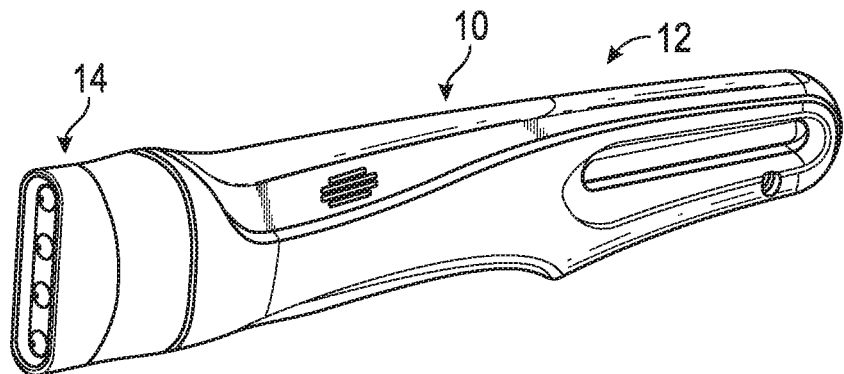

Advantageously, in some embodiments, head 14, or at least the needle portion thereof, is detachable and replaceable from the handpiece 12. This feature is shown in FIGS. 13-14. In use, head 14 may be replaced at the same time cartridge (not shown in FIGS. 14-16) is replaced, for example, after a certain number of injections, thus providing new, sharp needles for each subsequent use. For example, head 14 is detachable from handpiece 12, and can be replaced with another head, for example, an identical head, by rotating head 14 with respect to handpiece 12. This may be accomplished in a number of ways, for example, the device 10 may be structured such that replacing head 14 comprises the steps of manually placing head 14 onto handpiece 12 at 90° out of alignment therewith, and subsequently twisting or rotating head 14 clockwise 90° into alignment to lock it in place on handpiece 12. Removing head 14 may be accomplished, for example, by performing the steps in reverse.

In the shown embodiment, head 14 is separable from a distal hub 112 portion of handpiece 12 which houses dosing block, dosing spring, and dosing manifold. Thus, in this particular example, head 14, including the needle array housing assembly 32, needles 22, needle hub and needle assembly spring, as described and shown elsewhere herein, is replaceable with respect to the handpiece 12. In alternative embodiments, replaceable components may include one or more components or portions of the dosing manifold or distribution manifold. Needles 22 may be in a retracted position when the head 14 is separated from handpiece 12. Distal hub 112 may include coupling threads 114 or other suitable structure, for engaging mating threads or other structure (not shown) within head 14.

Methods of using device 10 for treatment or improvement of skin are also provided. For example, a method comprises providing a device such as described and shown herein.

A user, for example, a physician or an aesthetician, selects a region of skin to be treated on a patient. Potential skin regions that may benefit by treatment with device include the entire face, or portions thereof, including the forehead, the cheek, the nose, and the chin, the neck, the décolletage, the shoulders, the back, and any other region of skin that would benefit from improved hydration, elasticity, improved texture, and reduced fine lines and depressions.

The head of the device is placed into contact with a boundary of the selected area of skin to be treated. The user activates the device, for example, by pressing trigger. While the device remains in contact with the skin, one aliquot of composition is delivered into the area, simultaneously from each of the needles, at spaced apart injection points. Thus, when using the exemplary device shown and described, four aliquots or doses of composition are delivered simultaneously into the skin at about 10 mm apart, at a depth of about 0.5 mm to about 3.0 mm, for example, about 1 mm. While the device is still positioned against the skin, the user releases the trigger and the needles are retracted from the skin. Once the needles have retracted, the user moves the device laterally to an adjacent region of the skin, and the user again activates the device, delivering another set of doses.

Interestingly, the structure of the present device allows the user to maintain the device in contact with the skin during the treatment and between trigger presses. Because the needles retract into the head and behind the distal-most region of the head (such as shown in FIGS. 2 and 6) instead of lifting the device between subsequently delivered doses, the user may safely slide the device head on the skin to the next portion of skin in the treatment region before pressing the trigger to deliver the next set of doses.

The device may be structured to reduce or mitigate pain or anxiety in the patient. As mentioned above, the structure of the present invention, for example, when used as described, provides squeeze/slide action over the face or other treatment region. This feature may improve the comfort of the patient's experience, for example, in that the patient is not subjected to repeated lifting and contact of the device head on her skin, which may be relatively unpleasant to the patient and cumbersome to the physician. For example, when being treated with the present device, the patient may experience the treatment as a continuous, rather smooth, uninterrupted process, even between trigger presses, as the device maintains contact with the skin rather than the device needing to be repeatedly lifted and reapplied. Furthermore, the structure of the device provides an additional advantage in that it enables doses to be delivered without need to press the needles, or even the device head, into the skin. The doses are delivered by rapid trigger action as described herein, while the device is in gentle contact with the skin. Advantageously, the conical portions 44 described elsewhere herein may also provide some pain relief to the patient, by preloading or stretching the skin immediately prior to the injection, thereby possibly reducing or mitigating pain caused by the needle prick. In a similar respect, it is also contemplated to be within the scope of the invention to provide a vibrating motor on the device, effective to cause the head to vibrate when applied to the skin, thereby also mitigating pain of injection.

In some embodiments, the dose delivered from the sum of the needles, that is, from the plurality of needles in sum, e.g. during a single trigger pull, is for example about 1 ml, or about 2 ml, or about 3 ml, or about 4 ml or about 5 ml. In some embodiments, the dose delivered from the sum of the needles, is between about 10 µl to about 2 ml. In some embodiments, the dose delivered from the sum of the needles is between about 20 µl and about 1 ml. In some embodiments, the dose delivered from the sum of the needles is about 10 µl, about 20 µl, about 30 µl, about 40 µl, about 50 µl, about 60 µl, about 70 µl, about 80 µl, about 90 µl, about 100 µl, about 120 µL about 140 µL, about 160 µL, about 180 µL, about 200 µL, about 300 µL about 400 µL, or about 500 µL, or greater.

Again, by way of example only, in some embodiments, the dose delivered per needle of the plurality of needles, e.g. during a single trigger pull, is between about 2 µl and about 100 µl, between about 2 µL to about 200 µl, or between about 2 and about 300 µL. In some embodiments, the dose delivered per needle per trigger pull is, for example, between about 5 µL, to about 100 µL, from about 10 µL to about 80 µL, or from about 40 µL to about 60 µL. In some embodiments, the dose delivered per needle per trigger pull is between about 5 µl and about 50 µl, for example, between about 10 µl and about 40 µl per needle. In some embodiments, the device is capable of providing doses from each needle tip in an amount of about 6 µl, about 8 µl, about 10 µl, about 12 µl, about 14 µl, about 16 µl, about 18 µl, about 20 µl, about 22 µl, or about 24 µl, or greater. For example, in some embodiments, the device is capable of providing doses from each needle tip of about 30 µL, about 40 µL, about 50 µL, about 60 µL, about 70 µL, about 80 µL, about 90 µL, about 100 µL, or greater. In some embodiments, the dose delivered per needle per trigger pull is less than about 200 µL, less than about 100 µL, less than about 50 µL, less than about 25 µL, less than about 10 µL, or less than about 5 µL.

In one embodiment (e.g. a four needle embodiment), the device is structured to be capable of delivering 40 µL of composition, per trigger pull, by way of 4 spaced-apart, simultaneously injections of 10 µL. In another embodiment, (e.g. a ten needle embodiment), the device is capable of delivering 100 µL of composition, per trigger pull, by way of 10 spaced-apart, simultaneously injections of 10 µL. In another embodiment, (e.g. an eight needle embodiment), the device is capable of delivering 40 µL of composition, per trigger pull, by way of eight spaced-apart, simultaneously injections of 5 µL. In yet another embodiment (e.g. another ten needle embodiment), the device is capable of delivering 200 µL of composition, per trigger pull, by way of 10 spaced-apart, simultaneously injections of 20 µL. In yet a still further another embodiment (e.g. another ten needle embodiment), the device is capable of delivering 20 µL of composition, per trigger pull, by way of 10 spaced-apart, simultaneously injections of 2 µL. In still another embodiment (e.g. a 20 needle embodiment), the device is capable of delivering 400 µL of composition, per trigger pull, by way of 20 spaced-apart, simultaneously injections of 20 µL. In another embodiment (e.g. a two needle embodiment), the device is capable of delivering 200 µL of composition, per trigger pull, by way of 2 spaced-apart, simultaneously injections of 100 µL. These are some examples of various embodiments of the invention, and are not intended to limit the scope of the invention.

In yet other embodiments, the device enables treatment of a skin surface in a reduced amount of time, relative to conventional devices and techniques, for example, relative to treatment of a region of the same size using a standard needle and syringe. For example, in some embodiments, the device is capable of delivering about 1 ml to about 2 ml of a fluid into skin in depots of 5 µL to about 100 for example, in a time of about 45 minutes, about 30 minutes, about 20 minutes, about 15 minutes, or about 10 minutes.

The device may be structured such that a desired depth of injection is achieved, for example, to achieve a target depth in the epidermis, dermis or the hypodermis. It will be appreciated that the desired depth of injection may be at least somewhat dependent on the area of skin being treated, and/or the desired aesthetic or therapeutic effect to be achieved.

Embodiments of the invention include needle lengths, for example, lengths of between about 2 mm to about 20 mm, for example, a needle having a length of about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm, or other length suitable for delivering composition at a desired depth. In some embodiments, the needle gauge is 18 G, 22 G, 25 G, 27 G, or 30 G or thinner. In some embodiments, the needle gauge is at least 27 G up to about 34 G, for example, 30 G, 32 G, 33 G, or 34 G.

By way of example, the device may be structured to achieve treatment of skin by injection of composition at a very shallow level, for example, at a depth of about 0.1 mm or about 0.5 mm to about 2 mm or about 3 mm, into the epidermis. In other embodiments, deeper injection into the skin may be achieved. For example, in some embodiments, the depth of injection is between about 2 mm to about 4 mm. Even deeper injections may be between about 4 mm to about 10 mm, or even about 12 mm to about 15 mm in depth. In some embodiments, the depth of injection is about 0.5 mm to about 2 mm. In other embodiments, the depth of injection is about 4 mm to about 10 mm. In other embodiments, the depth of injection, is about 5 mm to about 12 mm.

Methods for using the device may include the step of moving the device along the skin between doses so as to effect subsequent, spaced apart doses so as to treat a desired surface area of skin with spaced apart injections. In some embodiments, the method includes delivering subsequent doses (each dose including delivery of composition from the plurality of needles) at spaced apart regions of the skin. For example, in some embodiments, the doses are spaced apart by about 5 mm and about 20 mm, for example, wherein the doses are spaced apart by about 10 mm, or about 15 mm. By thus moving the device along the skin between trigger pulls, a large surface area of skin can be treated by closely spaced apart injections.

Example

For the sake of simplicity, the following example, refers to a four-needle device, for example, device 10, but it should be appreciated that a similar sequence of steps can be used, mutatis mutandis, with other embodiments of the invention, which include, for example, different numbers and/or arrangements of needles.

A 43-year old woman complains to her dermatologist that she is dissatisfied with the appearance of her face, and more specifically, her skin. The dermatologist observes that the woman's facial skin, while having relatively few wrinkles and lines that are common to women her age, appears dry and blotchy, and the texture irregular, with highly visible pores and old acne scars in the form of shallow depressions.

The physician explains to the woman that a traditional dermal filler treatment would be helpful to fill in the few, and mostly insignificant, wrinkles, but that such traditional dermal filler treatment would not necessarily provide what she is looking for, that is, an improvement in the overall appearance of her skin, e.g. restoration of a youthful glow, decreased dryness, and improvement in texture and smoothness. The dermatologist recommends a microinjection treatment using a device (e.g. device 10) as described herein, to introduce, through multiple shallow injections, a hyaluronic-based composition, which may contain vitamins, antioxidants and/or other beneficial ingredients. The patient agrees to undergo the treatment.

Beginning near the jawline of the patient, the dermatologist gently places the distal end of the device on the skin. Without pressing the device into the skin, e.g. any more than is necessary to simply maintain gentle contact therewith, the physician presses the trigger. Four doses of composition are simultaneously delivered from the needles shallowly into the skin. Each needle delivers a single drop of the composition, for example, about 10 μl. A single trigger squeeze delivers therefor about 40 μl of the composition (4×10 μl) into a region of skin about 40 mm in length. The depth of the injection is between about 0.5 mm and about 3 mm. The needles automatically retract. While retaining contact with the skin, the dermatologist slides the device laterally along the face, a distance of only about 5 to about 10 mm, and again presses the trigger. A second injection is administered, e.g. another 40 μl provided through the four needles. The dermatologist repeats the slide and trigger action until the region of skin has been treated with multiple, shallow injections of small drops of the composition. After 25 trigger pulls, or in other words, 25 deliveries of 40 μl doses (4×10 μl), about 1 ml of composition has been delivered to the skin (40 μl×25=1 ml).

The physician next ejects the spent cartridge from the device, and replaces it with a new full 1.0 ml cartridge (see FIG. 16). The dermatologist also removes and replaces original, spent head with a new, unused head 14 (see FIG. 13-15), the new head having brand new, sharp needles (the needles of original head having become dull from the 25 injections). The dermatologist repeats the treatment on the other portion of the patient's face using the new head and a new cartridge. This process is repeated until the full skin area is treated as desired. The procedure is relatively painless and fast, and takes only about 20 to about 45 minutes. The patient is told to wear sunscreen when she is outdoors and to drink plenty of water over the next few days to protect her newly treated skin.

Within several days of treatment, the patient notices a visible improvement of her complexion. Her skin is noticeably suppler and less dry, more hydrated. The minute acne scar depressions are nearly gone, and her pores appear less visible. She returns to the dermatologist for a follow up treatment every 6 weeks, and tells him she is pleased that her face has a more youthful glow.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A dermal filler injection device comprising:
   a handpiece comprising:
      a handpiece housing including an interior space for containing a cartridge having a plunger slidable within the cartridge; and
      a trigger coupled to the housing;
   a head, in communication with the interior space, the head comprising a needle array housing assembly and a needle hub disposed within the needle array housing assembly and a plurality of needles secured to the needle hub; and
   a plurality of dosing chambers, wherein a lumen of each needle is in communication with a corresponding dosing chamber,
   wherein the device is structured such that operation of the trigger initially causes the plurality of needles to be moved from a retracted position to an extended position; and
   wherein the head being manually separable from, and replaceable with respect to, the handpiece.

2. The device of claim 1, wherein the plurality of dosing chambers is disposed in the handpiece.

3. The device of claim 1, wherein radial compression to the trigger is configured to cause distal advancement of the plunger relative to the cartridge disposed within the housing to cause a dose of composition contained in each dosing chamber to be delivered.

4. A dermal filler injection device comprising:
   a housing including an interior space for containing a cartridge;
   a trigger coupled to the housing;
   a head in communication with the interior space and including a plurality of dosing chambers, and a plurality of retractable needles coupled thereto;
   wherein the device is structured such that operation of the trigger initially causes the plurality of needles to be moved from a retracted position to an extended position and subsequently causes a dose of fluid contained in each of the dosing chambers to be ejected from a respective lumen of each of the needles when each needle is in the extended position; the device further structured to cause retraction of the needles after the dosing; and
   a mechanism capable of filling each dosing chamber between subsequent injections.

5. The device of claim 4, wherein the plurality of needles comprises adjacent needles spaced apart by at least about 10 mm.

6. The device of claim 4, wherein the plurality of needles comprises adjacent needles spaced apart by less than 10 mm.

7. The device of claim 4, wherein the plurality of needles comprises adjacent needles spaced apart by about 3 mm to about 14 mm.

8. The device of claim 4, wherein the plurality of needles comprises linearly arranged needles.

9. The device of claim 4, wherein the plurality of needles comprises at least four linearly arranged needles.

10. The device of claim 4, wherein the plurality of needles comprises a two by two array of needles.

11. The device of claim 4, wherein the head further includes a plurality of conical or tapered projections, each needle having a tip protruding from an individual conical or tapered projection.

12. The device of claim 11, wherein each conical or tapered projection is spaced apart from each other conical or tapered projections so as to effect a preloading of skin when the head is applied to skin, to facilitate penetration of the needle tips into the skin.

* * * * *